US005681559A

United States Patent [19]

DiGiusto et al.

[11] Patent Number: 5,681,559

[45] Date of Patent: Oct. 28, 1997

[54] METHOD FOR PRODUCING A HIGHLY ENRICHED POPULATION OF HEMATOPOIETIC STEM CELLS

[75] Inventors: David DiGiusto; Anne Galy, both of Palo Alto, Calif.

[73] Assignee: Systemix, Inc., Palo Alto, Calif.

[21] Appl. No.: 474,208

[22] Filed: Jun. 6, 1995

Related U.S. Application Data

[63] Continuation of Ser. No. 112,603, Aug. 25, 1993, abandoned.

[51] Int. Cl.$^6$ .............................. C12N 15/00; C12N 5/00; A01N 63/00; G01N 33/567

[52] U.S. Cl. .................... 424/93.1; 424/93.7; 435/172.3; 435/240.2; 435/7.2; 435/7.21

[58] Field of Search ................................ 424/93.1, 93.21

[56] References Cited

U.S. PATENT DOCUMENTS 5,035,994 7/1991 Civin .
5,061,620 10/1991 Tsukamoto et al. .

OTHER PUBLICATIONS

Civin et al., "Antigenic analysis of hematopoiesis III. A hematopoietic progenitor cell surface antigen defined by a monoclonal antibody raised against KG–1 a cells" *J. Immunol.* (1984) 133:157–165.

Berenson et al., "Engraftment after infusion of CD34$^+$ marrow cells in patients with breast cancer or neuroblastoma" *Blood* (1991 ) 77:1717–1722.

Terstappen et al., "Sequential generations of hematopoietic colonies derived from single nonlineage–committed CD34$^+$ CD38$^-$ progenitor cells" *Blood* (1991) 77:1218–1227.

Teixidó et al., "Role of $\beta_1$ and $\beta_2$ integrins in the adhesion of human CD34$^{hi}$ stem cells to bone marrow stroma" *J. Clin. Invest.* (1992) 90:358–367.

Brandt et al., "Characterization of a human hematopoietic progenitor cell capable of forming blast cell containing colonies in vitro" *J. Clin. Invest.* (1988) 82:1017–1027.

Lansdorp et al., "Long–term erythropoiesis from constant numbers of CD34$^+$ cells in serum–free cultures initiated with highly purified progenitor cells from human bone marrow" *J. Exp. Med.* (1992) 175:1501–1509.

Baum et al., "Isolation of a candidate human hematopoietic stem–cell population" *Proc. Natl. Acad. Sci. USA* (1992) 89:2804–2808.

Terstappen et al., "Flow cytometric assessment of human T–cell differentiation in thymus and bone marrow" *Blood* (1992) 79:666–677.

Andrews et al., "Monoclonal antibody 12–8 recognizes a 115–kd molecule present on both unipotent and multipotent hematopoietic colony–forming cells and their precursors" *Blood* (1986) 67:842–845.

Andrews et al., "Human hematopoietic precursors in long–term culture: single CD34$^+$ cells that lack delectable T cell, B cell and myeloid cell antigens product multiple colony–forming cells when cultured with marrow stromal cells" *J. Exp. Med.*. (1990) 172:355–358.

Barry et al., "Successful engraftment of human postnatal thymus in severe combined immune deficient (SCID) mice: differential engraftment of thymic components with irradiation versus anti–asialo GM–1 immunosuppressive regimens" *J. Exp. Med.* (1991) 173:167–180.

Berenson et al., "Antigen CD34$^+$ marrow cells engraft lethally irradiated baboons" *J. Clin. Invest.* (1988) 81:951–955.

Civin et al., "Cell surface antigens on human marrow cells: dissection of hematopoietic development using monoclonal antibodies and multi–parameter flow cytometry" *Int. J. Cell. Cloning* (1987) 5:267–288.

Hendrickson et al., "A link between double–strand break–related repair and V(D)J recombination: the scid mutation" *Proc. Natl. Acad. Sci. USA* (1991) 88:4061–4065.

Huang et al., "Formation of hematopoietic microenvironment and hematopoietic stem cells from single human bone marrow stem cells" *Nature* (1992) 360:745–749.

Kyoizumi et al., "Implantation and maintenance of functional human bone marrow in SCID–hu mice" *Blood* (1992) 79:1704–1711.

Lansdorp et al., "CD34 epitopes" in Knapp, W., et al., (eds.) *Epitopes: Leukocyte Typing IV. White Cell Differentiation Antigens* (1989) pp. 826–827.

Lansdorp et al., "Selective expression of CD45 isoforms on functional subpopulations of CD34$^+$ hematopoietic cells from human bone marrow" *J. Exp. Med.* (1990) 172:363–366.

Leary et al., "Blast cell colony assay for umbilical cord blood and adult bone marrow progenitors" *Blood* (1987) 69:953–956.

Lefkovits et al., "Limiting dilution analysis of cells of the immune system I. The clonal basis of the immune response" *Immunology Today* (1984) 5:265–268.

Lu et al., "Characterization of adult human marrow hematopoietic progenitors highly enriched by two–color cell sorting with MY10 and major histocompatibility class II monoclonal antibodies" *J. Immunol.* (1987) 139:1823–1829.

Namikawa et al., "Long term human hematopoiesis in the SCID–hu mouse" *J. Exp. Med.* (1990) 172:1055–1063.

Noble et al., "The 0–2A (adult) progenitor cell: a glial stem cell of the adult central nervous system" *Semin. Cell Biol.* (1992) 3:413–422.

Overton, "Modified histogram subtraction technique for analysis of flow cytometry data" *Cytometry* (1988) 9:619–626.

Péault et al., "Lymphoid reconstitution of the human fetal thymus in SCID mice with CD34$^+$ precursor cells" *J. Exp. Med.* (1991) 174:1283–1286.

(List continued on next page.)

*Primary Examiner*—Suzanne E. Ziska
*Attorney, Agent, or Firm*—Morrison & Foerster LLP

[57] ABSTRACT

The present invention provides a simple and reliable means for isolating populations of hematopoietic cells enriched for stem cell activity on the basis of possession of high CD34 cell surface antigen density ("CD34hi"). CD34$^{hi}$ cell preparations are useful, for example, for drug discovery efforts, for reconstituting hematopoiesis in an animal lacking a functioning hematopoietic system, and for gene therapies.

17 Claims, 13 Drawing Sheets

OTHER PUBLICATIONS

Ploemacher et al., "An in vitro limiting–dilution assay of long–term repopulating hematopoietic stem cells in the mouse" *Blood* (1989) 74:2755–2763.

Simmons et al., "Identification of stromal cell precursors in human bone marrow by a novel monoclonal antibody, STRO–1" *Blood* (1991) 78:55–62.

Simmons et al., "CD34 expression by stromal precursors in normal human adult bone marrow" *Blood* (1991) 78:2848–2853.

Spangrude et al., "Differentiation of hematopoietic stem cells in irradiated mouse thymic lobes: kinetics and phenotype of progeny" *J. Immunol.* (1990) 145:3661–3668.

Strauss et al., "Antigenic analysis of hematopoiesis. V. Characterization of My–10 antigen expression by normal lymphohematopoietic progenitor cells" *Exp. Hematol.* (1986) 14:878–886.

Sutherland et al., "Characterization and partial purification of human marrow cells capable of initiating long–term hematopoiesis in vitro" *Blood* (1989) 74:1563–1570.

Sutherland et al., "Functional characterization of individual human hematopoietic stem cells cultured at limiting dilution on supportive marrow stromal layers" *Proc. Natl. Acad. Sci. USA* (1990) 87:3584–3588.

Sutherland et al., "Differential regulation of primitive human hematopoietic cells in long–term cultures maintained on genetically engineered murine stromal cells" *Blood* (1991) 78:666–672.

Tindle et al., "A novel monoclonal antibody B1–3C5 recognizes myeloblasts and non–B non–T lymphoblasts in acute leukemias and CGL blast crisis and reacts with immature cells in normal bone marrow" *Leuk. Res.* (1985) 9:1–9.

Watt et al., "Distribution and epitope analysis of the cell surface membrane glycoprotein (HPCA–1) associated with human hematopoietic progenitor cells" *Leukemia* (1987) 1:417–426.

Weilbaecher et al., "Culture of phenotypically defined hematopoietic stem cells and other progenitors at limiting dilution on dexter monolayers" *Blood* (1991) 78:945–952.

Williams et al., "Characterization of hematopoietic stem and progenitor cells" *Immunol. Res.* (1987) 6:294–304.

Brenner, "Gene transfer into human hematopoietic progenitor cells: A review of current clinical protocols" *J. Hematother.* (1993) 2:7–17.

Moore et al., "Analysis of gene transfer in bone marrow cells" *Gene Targeting,* Practical Approach Series, Joyner, A.L. (ed.), IRL Press, New York, (1993) Chapter 3, pp. 63–106.

Lim et al., "Retrovirus–mediated gene transfer of human adenosine deaminase: Expression of functional enzyme in murine hemopoietic stem cells in vivo" *Mol. Cell. Biol.* (1987) 7:3459–3465.

Lu et al Blood 81(1): 41, 1993.

| STEM CELL PRECURSOR FREQUENCY IN FETAL BONE MARROW SUBPOPULATIONS | | | | | | |
|---|---|---|---|---|---|---|
| | CD34+/LIN- | | | CD34-/LIN- | | |
| TISSUE ID | WEEK 4 | WEEK 5 | WEEK 6 | WEEK 4 | WEEK 5 | WEEK 6 |
| L309 | 0.253% | 0.299% | 0.395% | 0.003% | 0.008% | 0.005% |
| L316 | 0.145% | 0.137% | | 0.003% | 0.003% | |
| L321 | 0.126% | 0.066% | 0.080% | 0.003% | 0.003% | 0.003% |
| L323 | 0.170% | 0.021% | | 0.003% | 0.021% | |
| L330 | 0.154% | 0.102% | 0.047% | 0.003% | 0.003% | 0.003% |
| K1022 | 0.082% | 0.065% | 0.073% | 0.003% | 0.003% | 0.003% |
| AVG | 0.155% | 0.115% | 0.149% | 0.003% | 0.007% | 0.004% |
| SD | 0.052% | 0.089% | 0.143% | 0.000% | 0.007% | 0.001% |
| 1/AVG= | 646 | 869 | 672 | 30000 | 14216 | 27369 |
| | CD34HI/LIN- | | | CD34LO/LIN- | | |
| L316 | 0.314% | 0.292% | 0.339% | 0.034% | 0.003% | 0.029% |
| L321 | 0.571% | 0.275% | 0.316% | 0.003% | 0.003% | 0.003% |
| L323 | 0.513% | 0.021% | | 0.070% | 0.021% | |
| L341 | 0.385% | 0.426% | 0.833% | 0.003% | 0.003% | 0.003% |
| L345 | 0.909% | 0.602% | 0.355% | 0.045% | 0.028% | 0.048% |
| K1022 | 0.441% | 0.457% | 0.172% | 0.003% | 0.006% | 0.009% |
| AVG | 0.522% | 0.345% | 0.403% | 0.027% | 0.011% | 0.018% |
| SD | 0.210% | 0.199% | 0.251% | 0.028% | 0.011% | 0.019% |
| 1/AVG= | 192 | 289 | 248 | 3754 | 9161 | 5410 |

METHOD FOR PRODUCING A HIGHLY ENRICHED POPULATION OF HEMATOPOIETIC STEM CELLS

This application is a continuation of application Ser. No. 08/112,603, filed Aug. 25, 1993, now abandoned.

DESCRIPTION

1. Technical Field

This invention is related to the isolation of a cell population enriched in hematopoietic stem cells.

2. Background Art

Mammalian hematopoietic cells are responsible for an extraordinarily diverse range of activities. They are divided into several lineages, including lymphoid, myeloid and erythroid. The lymphoid lineage, comprising B cells and T cells, produces antibodies, regulates cellular immunity, and detects foreign agents such as disease-causing organisms in the blood. The myeloid lineage, which includes monocytes, granulocytes, and megakaryocytes, monitors the blood for foreign bodies, protects against neoplastic cells, scavenges foreign materials, and produces platelets. The erythroid lineage includes red blood cells, which carry oxygen.

Despite the diversity in the morphology, function, and other characteristics of these cells, a single cell type called the hematopoietic "stem cell" is believed to act as the progenitor of all hematopoietic lineages. These rare primitive cells (approximately 0.01% of bone marrow cells) are distinguished by their high proliferative potential and possible self renewal. Stem cells differentiate into multipotent progenitor cells and ultimately into each of the mature hematopoietic lineages. Thus, stem cells are believed to be capable of generating long-term hematopoiesis when transplanted into immunocompromised hosts.

The stem cell was originally defined by the capacity to self-renew and to give rise to progeny that are the committed precursors for all hematopoietic lineages. A number of researchers have concluded from their attempts to divide the progenitor cell compartment into stem cell and committed progenitor cells that these compartments constitute a hierarchy or continuum of cell types whose maturation is characterized by decreasing pluripotentiality and by a decreasing ability to repopulate the hematopoietic system of serially transplanted animals.

Strategies for isolating stem cells typically seek to exploit differences in cell size or density or the selection or depletion of cells based on the expression of cell surface antigens. It has been difficult, however, to identify and purify stem cells because of the small proportion of stem cells in the bone marrow, peripheral blood, and other sources. In addition, many cell surface markers associated with stem cells are also present on more differentiated cells.

CD34, for example, is thought to be present on all human hematopoietic progenitor cells (Civin et al. (1984) *J. Immunol.* 133:157–165), and this population can mediate engraftment of an immunocompromised host in vivo (Berenson et al. (1991) *Blood* 77:1717–1722). Although the presence of primitive hematopoietic cells expressing relatively high CD34 density has been reported (Berenson et al. (1991); Terstappen et al. (1991) *Blood* 77:1218–1227; Teixido et al. (1992) *J. Clin. Invest.* 90:358–367), the $CD34^+$ cell population is heterogeneous with respect to the types of progenitor cells and their relative state of differentiation (Terstappen et al. (1991)) and the fraction of the $CD34^+$ compartment containing hematopoietic stem cells has not been consistently and reliably defined.

Previously described schemes for obtaining stem cells require the sequential isolation of subpopulations of $CD34^+$ cells which either have additional cell surface antigens associated with stem cells or lack other antigens associated with committed cells. Several schemes to fractionate human hematopoietic cells into lineage committed and non-committed progenitors have been reported (see, e.g., Berenson et al., 1991; Terstappen et al., 1991; Brandt et al. (1988) *J. Clinical Investigation* 82:1017–1027; Landsdorp and Dragowska (1992) *J. Exp. Med.* 175:1501–1509; Baum et al. (1992) *Proc. Natl. Acad. Sci.* 89:2804–2808). Such methods are technically complicated and may at times not permit the recovery of enough stem cells to address multi-lineage differentiation along the different lymphoid pathways. The sequential fractionation steps may under certain circumstances result in dramatic reductions in stem cell yield from a cell population which contains only a minuscule fraction of stem cells to begin with.

The relative paucity of hematopoietic stem cells has prevented extensive research on stem cells and hematopoietic differentiation in general. The ready availability of a cell population enriched in hematopoietic stem cells would make possible the identification of biological modifiers affecting stem cell behavior. For example, there may be as yet undiscovered growth factors associated with (1) early steps of dedication of the stem cell to a particular lineage; (2) the prevention of such dedication; and (3) the ability to control stem cell proliferation.

The availability of sufficient numbers of stem cells in an enriched population would also be extremely useful, for example, in reconstituting hematopoiesis in patients undergoing treatments which destroy stem cells, such as cancer chemotherapy. Stem cells are also important targets for gene therapy.

DISCLOSURE OF THE INVENTION

The present invention provides methods for obtaining cell populations, preferably human cells, especially fetal cells, enriched in hematopoietic stem cells selected on the basis of possession of mean fluorescence values (MFV) for CD34 surface antigen approximately 100 times or more than that of isotype controls.

Also provided are compositions obtained by such methods. These compositions are useful, for example, in reconstituting hematopoiesis in an animal lacking a functioning hematopoietic system. These compositions are also useful for treating an animal affected by a genetic disease comprising introducing into the animal a $CD34^{hi}$ cell transfected with a nucleic acid capable of either expressing in the transfected cell a polypeptide which is missing or defective in the animal or expressing a nucleic acid or polypeptide capable of inhibiting the expression of a target protein in the animal.

Also provided are methods for evaluating a sample for the presence of a biological modifier capable of affecting a biological response of a hematopoietic stem cell, the method comprising plating a test $CD34^{hi}$ cell (with the sample) and a control $CD34^{hi}$ cell (without the sample) in an appropriate culture system and comparing the biological response of the test and control $CD34^{hi}$ cells.

BRIEF DESCRIPTION OF THE DRAWINGS

FIG. 4 lists the precursor frequencies for sorted fetal bone marrow subpopulations as the percentage of cells that form cobblestone areas between weeks four and six in SyS-1 coculture as determined by limiting dilution analysis. Some cultures were either lost to contamination or sacrificed for analysis prior to week 6 (blank spaces). The average response (AVG) and standard deviation (SD) were calculated. The number of cells containing one cobblestone area-forming cell is listed as the reciprocal of the average frequency (1/AVG).

MODES FOR CARRYING OUT THE INVENTION

The present invention provides a method for isolating a population of hematopoietic cells highly enriched for stem cells by separating two distinct populations of $CD34^+$ cells, one expressing high levels of CD34 antigen ("$CD34^{hi}$") and the other expressing lower levels of CD34 antigen ("$CD34^{lo}$").

Initial studies had suggested that $CD34^+$ cells were enriched for stem cells (see, e.g., Civin, U.S. Pat. No. 5,035,994, "Human Stem Cells and Monoclonal Antibodies"). U.S. Pat. No. 5,061,620, "Human Hematopoietic Stem Cell" (Tsukamoto et al.), for example, stated that B cell and myeloid cell progenitors make up 80–90% of the $CD34^+$ population. Work by Terstappen et al. ((1992) *Blood* 79:666–677) has suggested that CD34 antigenic density decreases with maturation of hematopoietic cells and increased CD38 cell surface expression.

The presence of primitive hematopoietic cells expressing relatively high CD34 density has been reported for adult bone marrow. However, these studies failed to consistently and reliably define which fraction of the $CD34^+$ compartment contains hematopoietic stem cell activity. Cells expressing relatively high CD34 density have been defined, for example, as a fixed percentage of low density marrow cells (Berenson et al., 1991) or, apparently, as staining "brightly" against a relatively high background (Teixido et al., 1992). Such definitions do not indicate what the CD34 density is on the surface of the cells, and, since samples vary for CD34 content, these definitions suffer from inconsistency and imprecision.

Figure 1A:
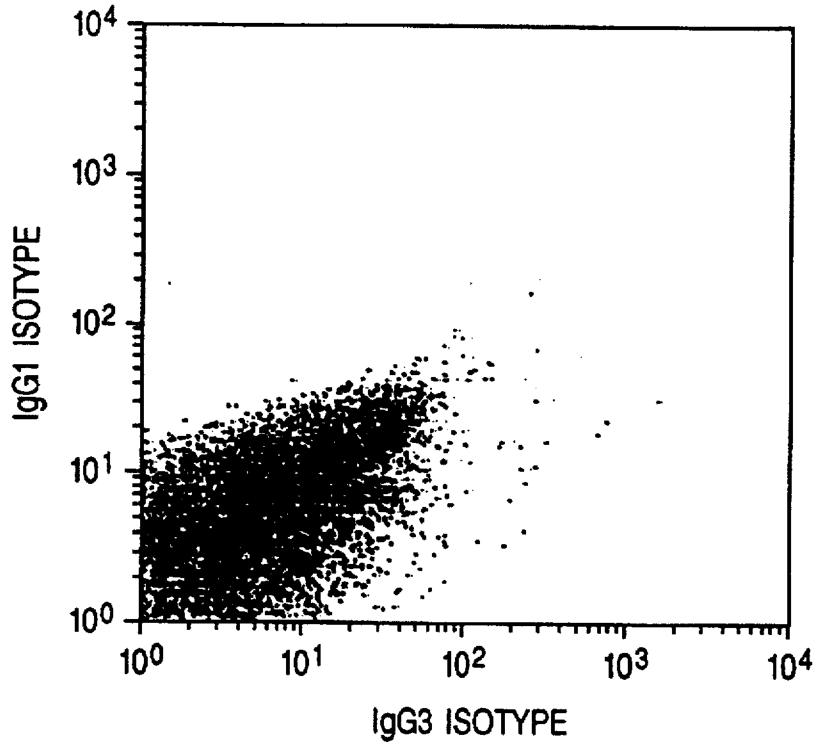
FIG. 1 shows the distribution of CD34 and lineage markers as determined by flow cytometry on an (A) isotype control and (B) on low density fetal bone marrow cells stained with anti-CD34 antibody (Tuk-3) and lineage antibodies (CD14, CD15, CD16).
FIG. 1(B) shows that there are two populations of $CD34^+$ cells, those expressing high levels of CD34 (arrow) and those expressing relatively low levels of CD34 (box).

It has been discovered that long-term multilineage potential representing hematopoietic stem cell activity is exclusively contained in a subset of $CD34^+$ cells, the "$CD34^{hi}$" population, distinguished by the expression of high levels of CD34 surface antigen. As shown in FIG. 1, in fluorescence activated cell sorting (FACS) scans of $CD34^+$ hematopoietic cells from fetal bone marrow, $CD34^{hi}$ cells reproducibly form a discrete population having approximately 100 times or more the mean fluorescence values for CD34 surface antigen of isotype controls (1.81 to 2.19 logs over isotype controls with an average of 2.07, n=9; see Table 2 below). Such cells have been found in all samples of fetal bone marrow tested.

An important distinction between these results and previous reports is that $CD34^+$ cells are being fractionated based on calculations related to relative CD34 antigen density and not by the mere percentage of $CD34^+$ cells in a cell population or another arbitrary cutoff. $CD34^{hi}$ cells are a discrete population of cells forming only about 2% of low density fetal bone marrow mononuclear cells. A simple single step fractionation of fetal bone marrow based on levels of CD34 expression provides a high yield of cells highly enriched in stem cell activity.

When $CD34^+$ cells are separated into the "high" and "low" fractions, the stem cells which serve as the progenitors for all human hematopoietic cell lineages are found exclusively in the $CD34^{hi}$ fraction. Long-term multilineage potential is exclusively contained in the $CD34^{hi}$ compartment. As shown in the examples below, a much higher percentage of $CD34^{hi}$ cells score positive in long term in vitro stromal coculture assays than for $CD34^+$ or $CD34^{lo}$ cells. Additionally, a higher percentage of $CD34^{hi}$ cells exclusively engraft into allogeneic fetal bone fragments implanted into severe combined immunodeficiency (SCID) mice and provide long term myelopoiesis and B-lymphopoiesis. Finally, more $CD34^{hi}$ cells differentiate into T cells in allogeneic thymus grafts implanted into SCID mice.

On the other hand, $CD34^{lo}$ cells do not display any significant long term activity in the generation of B cells or myeloid cells in vitro. Moreover, $CD34^{lo}$ cells are incapable of maintaining long term hematopoiesis in human bones and do not possess T cell progenitor activity. In short, all stem cell activity appears to be confined to the $CD34^{hi}$ cell population.

The analysis of a sufficient number of unrelated tissues demonstrated that the $CD34^{hi}$ population can be easily and reproducibly isolated in large numbers by fluorescence activated cell sorting, especially if a limited panel of antibodies to highly autofluorescent myeloid cells is used to increase resolution. High recoveries allowed extensive investigation of the biological properties of each population.

Phenotypic analysis of sorted populations showed that $CD34^{hi}$ cells were highly enriched for the phenotypes that have been reported to define the most primitive hematopoietic cells, such as $CD34^+$/Thy-$1^+$ (Baum et al., 1992), $CD34^+$/HLA-$DR^{lo}$ (Brandt et al. (1988); $CD34^+$/$CD38^{lo}$ (Terstappen et al., 1991), $CD34^+$/CD45 $RA^-$ (Landsdorp and Dragowska (1992). While these cells also express low levels of CD13 and CD33, which are found on multilineage progenitors, they do not bear cell surface antigens that define mature cells (CD2, CD10, CD14, CD15, CD16, CD19, or CD20).

On the other hand, $CD34^{lo}$ cells express antigens that suggest that they are activated progenitors for B and myeloid cells (CD10, CD19, and high levels of HLA-DR and CD38). $CD34^{lo}$ cells also do not express CD2; in that respect our data differ from what was reported by Terstappen et al. (1992), since we do not seem to identify a $CD34^+$/$CD2^+$ population in fetal bone marrow. The differential expression of lineage antigens on CD34 subsets underscores the fact that $CD34^{hi}$ cells form a biologically distinct population.

Isolation, further purification, and propagation of $CD34^{hi}$ cells

A $CD34^{hi}$ cell preparation is one which contains approximately 90% or more, and preferably 95% or more, $CD34^{hi}$ cells.

$CD34^{hi}$ cells are preferably prepared from fetal hematopoietic cell sources, e.g., bone marrow or liver, but may be purified from other fetal, neonatal, or adult hematopoietic cell sources, including bone marrow, fetal liver, embryonic yolk sac, fetal and adult spleen, and blood. Bone marrow cells may be obtained from the tibia, femur, spine, or other bone cavities.

The density of CD34 antigen in adult tissue is variable, depending on the differentiation state of any given cell in the sample. Clearly, CD34 negative cells (those expressing levels of CD34 antigen indistinguishable from the background) have no relevant progenitor or stem cell activity. $CD34^+$ cells express a range of antigen density much like that observed in fetal bone marrow, with the exception that the maximum CD34 antigen density for adult hematopoietic cells is somewhat less than that seen in fetal tissue, generally less than 100-fold higher than isotype controls. The adult cells having the highest cell surface density of CD34 do not form a clearly demarcated cell population on that basis alone, and thus a second marker is required to better define the population of cells possessing all hematopoietic stem cell activity.

$CD34^{hi}$ cells from fetal tissues have low levels of CD33 and CD38; intermediate levels of HLA-DR and CD13; and no appreciable CD14, 15, 16, glycophorin A. Stem cells are $Lin^-$. "$Lin^-$" refers to the absence or low expression of markers associated with lineage committed cells, including but not limited to, T cells (such as CD2, CD3 or CD8); B cells (such as CD10, 19 or 20); myelomonocytic cells (such as CD14, 15, 16); natural killer ("NK") cells (such as CD2) and red blood cells ("RBC") (such as glycophorin$^+$) megakaryocytes, mast cells, eosinophils and basophils.

Further fractionation of $CD34^{hi}$ cells to obtain greater enrichment in stem cell activity may be accomplished by any method known in the art. Phenotypes that have been reported in the literature to define the most primitive hematopoietic cells include $CD34^+$/Thy-$1^+$ (Tsukamoto et al., U.S. Pat. No. 5,061,620), $CD34^+$/HLA-$DR^{lo}$, $CD34^+$/$CD38^{lo}$, $CD34^+$/CD45 $RA^-$, and $CD34^+$/rhodamine $123^{lo}$.

$CD34^{hi}$ cells are preferably purified from fetal bone marrow or fetal liver. Other fetal, neonatal (particularly cord blood), or adult hematopoietic cell sources including bone marrow, liver, embryonic yolk sac, spleen, and blood may also be used. Bone marrow cells may be obtained from the tibia, femur, spine, or other bone cavities.

$CD34^+$ cells are easily and reproducibly fractionated into $CD34^{hi}$ and $CD34^{lo}$ cells based on CD34 antigen density on the cell surface. This is preferably accomplished by fluorescence activated cell sorting (FACS), especially FACS employing a limited panel of antibodies to highly autofluorescent myeloid cells to increase sorting resolution. See, e.g., *Flow Cytometry and Sorting*, ed. Melamed, Lindmo, and Mendelsohn, Wiley-Liss, Inc., 1990, especially the articles by Lindmo et al., pp. 145–169, and Visser, pp. 669–683.

A single step selection for $CD34^{hi}$ cells by flow cytometry, as described in the Examples below, will generally achieve an enriched $CD34^{hi}$ preparation having at least about 0.3% stem cells. Preferably, FACS, more preferably multi-color analysis using FACS, is employed to identify and/or select $CD34^{hi}$ cells present in a cell population. In a first separation, starting with at least about $1\times10^8$ and preferably at least about $1\times10^9$ cells, the antibody for CD34 may be labeled with one fluorochrome, while antibodies specific for the various dedicated lineages, if used, may be conjugated to a different fluorochrome. Fluorochromes which may find use in a multi-color analysis include, but are not limited to, phycobiliproteins, e.g., phycoerythrin and allophycocyanins, fluorescein and Texas red.

$CD34^{hi}$ cells may be further fractionated to achieve even more highly purified stem cell populations by subjecting a preparation of $CD34^{hi}$ cells to additional selection for cell surface markers (or other characteristics) associated with stem cells or against markers associated with lineage committed or mature hematopoietic cells. Additional selections may be performed in separate selection steps or several cell surface markers or may be selected for (or against) in a single step.

Although $CD34^{hi}$ cells are obtained by flow cytometry, a preliminary separation may be employed to remove lineage committed cells (e.g., T cells, pre-B cells, B cells, and myelomonocytic cells, or minor cell populations, such as megakaryocytes, mast cells, eosinophils and basophils) and enrich the cell population for $CD34^{hi}$ cells before directly selecting for $CD34^{hi}$ cells. Typically platelets and erythrocytes are removed prior to sorting. It is not essential to remove every dedicated cell class, particularly minor cell populations. Preferably at least about 70% and preferably at least 80% of the lineage committed or mature cells will be removed. Preliminary separations may conveniently be performed, for example, using magnetic beads coated with one or more specific monoclonal antibodies.

Dead cells may be selected against by employing such dyes as propidium iodide. Stem cells have low side scatter and low forward scatter profiles as determined by FACS analysis. Cytospin preparations show that stem cells have a size between mature lymphoid cells and mature granulocytes. Cells may be selected based on light-scatter properties as well as their expression of various cell surface antigens.

Monoclonal antibodies are particularly useful for identifying cell surface markers (membrane proteins exposed on the cell surface and readily identified, e.g., by specific antibodies) associated with particular cell lineages and/or stages of differentiation. The antibodies may be attached to a solid support to facilitate preliminary separation. The separation techniques employed should maximize the retention and viability of the fraction to be collected.

Antibodies employed for cell separations may be labeled by any method known in the art. Useful labels include, but are not limited to, fluorochromes, biotin, or other widely used labels. Alternatively, antibodies may be affixed to a solid support such as magnetic beads, which allow for direct separation.

The particular preliminary separation technique employed will depend upon efficiency, ease and speed of performance, and the need for sophisticated equipment and/or technical skill.

Among the techniques useful for preliminary separations are magnetic separation using antibody-coated magnetic beads, affinity chromatography with lectins or antibodies, cytotoxic agents joined to a monoclonal antibody or used in conjunction with a monoclonal antibody, e.g., complement and cytotoxins, and "panning" with antibody attached to a solid matrix. Separations can also be effected by exploiting differences in physical properties (e.g., density gradient centrifugation and counter-flow centrifugal elutriation) and vital staining properties (e.g., rho123 and Hoechst 33342). Techniques providing more accurate separation include, but are not limited to, FACS, which can have varying degrees of sophistication, e.g., a plurality of color channels, low angle and obtuse light scattering detecting channels, impedance channels, etc.

For isolation of bone marrow from fetal bone or other bone source, the bone may be flushed with an appropriate balanced salt solution, preferably supplemented with fetal calf serum (FCS) or other source of proteins, in conjunction with an acceptable buffer at low concentration, generally from about 5–25 mM. Convenient buffers include, but are not limited to, Hepes, phosphate buffers, and lactate buffers. Otherwise bone marrow may be aspirated from the bone in accordance with conventional methods.

When antibodies are used for positive or negative selection of $CD34^{hi}$ cells from bone marrow, the bone marrow cells are typically incubated for a short period of time at reduced temperatures, generally about 4° C., with saturating levels of antibodies specific for CD34 and/or other cell surface markers. The cells are then washed with a salt solution plus proteins and suspended in an appropriate buffered medium, then separated by means which recognize bound antibodies specific for particular cell surface antigens.

Isolated $CD34^{hi}$ cells may be propagated in a medium containing maintenance factors supporting the proliferation of stem cells, such as the growth factors secreted by stromal cells, which can be obtained from bone marrow, fetal thymus or fetal liver and which can be allogeneic or xenogeneic. For that reason, isolated $CD34^{hi}$ cells may be propagated by growth in media conditioned by stromal cells or by coculturing with stromal cells. Stromal cells used in such cocultures may be clonal cell lines, e.g., AC3, AC6, or, preferably SyS-1 (see Baum et al., "Long-Term In Vitro Lymphocyte Cultures," copending patent application U.S. Ser. No. 07/938,548, filed Aug. 28, 1992), or mixed stromal cell preparations derived from mouse or human fetal bone marrow from which hematopoietic cells have been removed. For example, hematopoietic cells can be removed by employing appropriate monoclonal antibodies conjugated with toxin, antibody and complement, etc., and then selecting for the ability to maintain human stem cells.

$CD34^{hi}$ cells may be frozen in liquid nitrogen and stored for long periods of time in 10% DMSO, 50% FCS, 40% RPMI 1640 medium. Once thawed, the cells may be grown in an appropriate culture system.

Uses for $CD34^{hi}$ cells

Among the uses of $CD34^{hi}$ cells are the following.

Drug discovery. $CD34^{hi}$ cells are useful for identifying culture conditions or biological modifiers such as growth factors which promote or inhibit such biological responses of stem cells as self-regeneration, proliferation, commitment, differentiation, and maturation. In this way one may also identify, for example, receptors for these biological modifiers, agents which interfere with the interaction of a biological modifier and its receptor, and polypeptides, antisense polynucleotides, small molecules, or environmental stimuli affecting gene transcription or translation.

One may use such assays as a strategy to identify and clone genes whose expression affects the self-regeneration, proliferation, commitment, differentiation, and maturation of stem cells or other hematopoietic cells.

In order to identify a biological modifier in a test sample, a $CD34^{hi}$ cell is plated as a single cell or in bulk culture in an appropriate culture system along with the test sample and allowed to expand to produce progeny cells. The proliferation, differentiation, and maturation of the $CD34^{hi}$ cell(s) is compared to that of a $CD34^{hi}$ cell(s) cultured under control conditions.

The capacity of stem cells in a $CD34^{hi}$ population to differentiate into various hematopoietic lineages may be demonstrated by culturing the cells under appropriate conditions, such as those described in the Examples. The cells are typically grown on mouse or human stromal cells. The medium employed for the culturing of stem cells for these purposes is preferably a defined enriched medium, such as IMDM (Iscove's Modified Dulbecco's Medium) or a 50:50 mixture of IMDM and RPMI (a commonly used medium whose name refers to "Roswell Park Memorial Institute"), and is generally composed of salts, amino acids, vitamins, $5\times10^{-5}$ M 2-mercaptoethanol (2-ME), streptomycin/penicillin at 100 μg/ml and 100 U/ml, respectively, and 10% FCS. The medium is typically changed from time to time, generally at least about once or twice per week.

The capacity of stem cells in a $CD34^{hi}$ population to differentiate into myeloid cells may be determined as set forth in the Examples below. Alternatively, Dexter-type cultures (containing hydrocortisone) are used; for production of B lymphocytes, Whitlock-Witte type cultures lacking hydrocortisone are used. The capacity to produce both myeloid cells and B lymphocytes may be demonstrated, for example, by culturing stem cells on an appropriate medium containing hydrocortisone and observing the production of myeloid cells, then transferring the cells to a culture lacking hydrocortisone and observing the production of B cells. Typically, the stem cell population to be tested is cultured for six weeks in a medium comprising a 50:50 mixture Of RPMI 1640 and IMDM containing 10% FCS, 10% horse serum, streptomycin/penicillin, glutamine and $5\times10^{-7}$ M hydrocortisone. In the absence of progenitor cells, all mature cells would be expected to die. If at the end of six weeks myeloid cells are observed, one may conclude that there were one or more progenitor cells in the culture which continuously differentiated into myeloid cells. One may then replace the medium with one lacking hydrocortisone to encourage the growth of B cells. After culturing the cells an additional 3–4 weeks, the presence of B cells indicates that the progenitor cells which were previously capable of producing myeloid cells are also capable of producing B cells. The presence of myeloid cells or B cells may conveniently be determined, for example, by FACS analysis.

To demonstrate the capacity of the stem cells to differentiate into T cells, isolated fetal thymus fragments are cultured for 4 to 7 days at about 25° C. in order to substantially deplete the thymus of its lymphoid population. Stem cells having human leukocyte antigen (HLA) mismatched with the HLA of the thymus cells are microinjected into the thymus tissue, which is then transplanted into a scid/scid mouse as described in EPA 0 322 240, preferably under the kidney capsule.

The capacity of the stem cells to differentiate into erythroid cells may be determined by conventional techniques to identify burst forming units-erythroid (BFU-E) activity, for example, methylcellulose culture (Metcalf (1977) in *Recent Results in Cancer Research* 61, Springer-Verlag, Berlin, pp. 1–227).

The present invention makes it possible to prepare relatively large numbers of hematopoietic stem cells for use in assays for the differentiation of stem cells into various hematopoietic lineages. These assays may be readily adapted in order to identify substances such as growth factors which, for example, promote or inhibit stem cell self-regeneration, commitment, or differentiation.

Identification of target antigens associated with a specific hematopoietic cell type. One may also use such cells to identify cell surface antigens or other target antigens present in, and preferably specific for, a given hematopoietic cell type. This may be accomplished, for example, by using the cell as an antigen for the production of monoclonal antibodies, which can be screened to obtain those monoclonal antibodies which are specific for the cell type. Such monoclonal antibodies would themselves be useful, e.g., for improved assays, for selecting for cells expressing their target antigen, or for purifying the target antigen itself.

Gene cloning strategies. One may also use such cells to identify and clone genes whose expression is associated with proliferation, commitment, differentiation, and maturation of stem cells or other hematopoietic cells, e.g., by subtractive hybridization or by expression cloning using monoclonal antibodies specific for target antigens associated with these biological events or characteristic of a hematopoietic cell type.

Reconstituting hematopoietic cells or providing cell populations enriched in desired hematopoietic cell types. The availability of $CD34^{hi}$ cells is also useful for reconstituting the full range of hematopoietic cells in an immunocompromised host following therapies including, but not limited to, radiation treatment or chemotherapy. Such therapies destroy hematopoietic cells either intentionally or as a side-effect of bone marrow transplantation or the treatment of lymphomas, leukemias and other neoplastic conditions, e.g., breast cancer.

$CD34^{hi}$ cells are useful as a source of cells for specific hematopoietic lineages. The maturation, proliferation and differentiation of $CD34^{hi}$ cells into one or more selected lineages may be effected through culturing the $CD34^{hi}$ cells with appropriate factors including, but not limited to, erythropoietin (EPO), colony stimulating factors, e.g., GM-CSF, G-CSF, or M-CSF, SCF, interleukins, e.g., IL-1, -2, -3, -4, -5, -6, -7, -8, -13, etc., or with stromal cells or other cells which secrete factors responsible for stem cell regeneration, commitment, and differentiation.

Gene therapy. $CD34^{hi}$ cells are also important targets for gene therapy. Expression vectors may be introduced into and expressed in autologous or allogeneic $CD34^{hi}$ cells, or the genome of $CD34^{hi}$ cells may be modified by homologous or non-homologous recombination by methods known in the art. In this way, one may correct genetic defects in an individual or provide genetic capabilities naturally lacking in stem cells. For example, diseases including, but not limited to, β-thalassemia, sickle cell anemia, adenosine deaminase deficiency, recombinase deficiency, and recombinase regulatory gene deficiency may be corrected in this fashion. Diseases not associated with hematopoietic cells may also be treated, e.g., diseases related to the lack of secreted proteins including, but not limited to hormones, enzymes, and growth factors. Inducible expression of a gene of interest under the control of an appropriate regulatory initiation region will allow production (and secretion) of the protein in a fashion similar to that in the cell which normally produces the protein in nature.

Similarly, one may express in a $CD34^{hi}$ cell a ribozyme, antisense RNA or protein to inhibit the expression or activity of a particular gene product. Drug resistance genes including, but not limited to, the multiple drug resistance (MDR) gene, may also be introduced into $CD34^{hi}$ cells, e.g., to enable them to survive drug therapy. For hematotrophic pathogens, such as HIV or HTLV-I, and HTLV II, the $CD43^{hi}$ cells can be genetically modified to produce an antisense RNA, ribozyme, or protein which would prevent the proliferation of a pathogen in $CD34^{hi}$ cells or differentiated cells arising from $CD34^{hi}$ cells. One may also disable or modulate the expression of a particular genetic sequence by methods known in the art, including, but not limited to, directly substituting, deleting, or adding DNA by homologous recombination or indirectly by antisense sequences.

The following examples are offered by way of illustration and not by way of limitation.

EXAMPLE 1

Fractionation of Fetal Bone Marrow Cells by CD34 Levels

Discussed below is a simple strategy for fractionation of fetal bone marrow which reproducibly segregates all of the stem cell activity and yet obtains a relatively large number of cells with which multiple experiments can be performed.

The following mouse monoclonal antibodies (mAbs) were used in these studies and those described below: anti-CD34 (Tuk-3) and FITC-labeled Fab'2 anti-Tuk3 (A. Ziegler, University of Berlin, Germany); FITC- or PE-conjugated anti-CD2 (Leu-5b), anti-CD20 (Leu-16), anti-CD19 (Leu-12), anti-CD-14 (Leu-M3), anti-CD15 (Leu-M1), anti-CD16 (Leu-11a), anti-CD33 (Leu-M9), Anti-CD4 (Leu-3a), anti-CD34 (HPCA-2) (Becton Dickinson, Mountain View, Calif.); FITC- or PE-conjugated anti-glycophorin A (D2.10) (AMAC, Westbrook, Me.); PE-conjugated RT6-CD1a (Coulter, Hialeah, Fla.); Tricolor (TC)-conjugated CD45, TC-CD8, TC-CD3 (Caltag, San Francisco, Calif.); anti-Thy 1.1 (GM201) (similar to that described in Dalchau and Fabre (1979) *J. Exp. Med.*, 149:576 was used); goat anti-mouse IgG1-PE antibody (Caltag, San Francisco, Calif.); FITC-conjugated anti-HLA antibodies MA2.1, BB7.2, GAP-A3, and PE-conjugated W6-32 anti-monomorphic class I MHC molecules were derived from hybridomas obtained at ATCC (Rockville, Md.); irrelevant mouse IgG1 (MOPC21) and irrelevant mouse IgG3 (FLOPC21) (Sigma, St. Louis, Mo.). For CD34 staining, Texas Red (TR)-conjugated polyclonal goat anti-mouse IgG3 (Southern Biotechnology Associates, Birmingham, Ala.) was used.

Staining and flow cytometry sorting of fetal bone marrow was performed as follows. Human fetal bones were dissected from 18 to 24 week-old fetuses obtained by elective abortion with informed consent (Advanced Bioscience Resources, Alameda, Calif. and International Institute for the Advancement of Medicine, Exton, Pa.). Marrow cell suspensions were prepared by flushing split long bones with RPMI containing 2% heat inactivated FCS. Low density (<1,077) mononuclear cells were isolated (Lymphoprep, Nycomed Pharma, Oslo, Norway), washed twice, then pre-incubated on ice in staining buffer (SB) (SB=Hanks' balanced salt solution+2% heat inactivated FCS, 10 mM HEPES) with i mg/ml heat inactivated human gamma-globulin (Gamimune, Miles, Elkhart, Ind.) to block Fc receptor binding of mouse antibodies. After 10 minutes, anti-CD34 mAbs or IgG3 isotype control mAbs were added at 0.7 μg per $10^6$ cells/0.1 ml SB for 20 minutes on ice. Cells were washed twice in SB, then incubated for 20 minutes with TR-conjugated goat anti-mouse IgG3 antibodies and FITC-labeled CD14, CD15, CD16 antibodies (hereafter referred to as "Lin") recognizing lineage-committed cells, followed by three washes in SB. Cells were resuspended in SB containing 1 μg/ml propidium iodide (Molecule Probes, Eugene, Oreg.) and sorted using the FACStar Plus cell sorter (Becton Dickinson, San Jose, Calif.). Live cells (i.e., those excluding propidium iodide) that were $Lin^-$ were sorted according levels of CD34 expression. Sort gates were set based on the mean fluorescence intensity of the isotype control sample. All cells with CD34 values between 10 and 100 times the mean fluorescence value of the isotype control were sorted as $CD34^{lo}$. Those cells with values for CD34 that were greater than 100 times the isotype control values were sorted as $CD34^{hi}$. Cells were collected in 24 or 48 well plates in RPMI with 2% FCS and 10 mM HEPES and were counted and reanalyzed for purity in every experiment.

Phenotypic analysis of low density fetal bone marrow revealed that $CD14^+$ monocytes, $CD15^+$ granulocytes, $CD16^+$ granulocytes, and natural killer (NK) cells together comprise an average of 40%±9% of all cells, and that these markers identified all highly autofluorescent cells and those with high orthogonal light scatter. These cells, as well as $CD2^+$ T-cells, $CD20^+$ B-cells, and glycophorin $A^+$ erythroblasts were distributed largely (>90%) into the $CD34^-$ compartment of the fetal bone marrow. $CD14^+$, $CD15^+$, and $CD16^+$ (i.e., $Lin^+$) cells expressed antigens associated with mature lineages and had no long term in vitro or in vivo hematopoietic activity.

Because the presence of autofluorescent and Fc-binding cells complicates flow cytometry analysis and sorting, $Lin^+$ cells were excluded from our FACS analysis by electronic gating without compromising the integrity of the $CD34^+$ compartment.

Figure 1B:
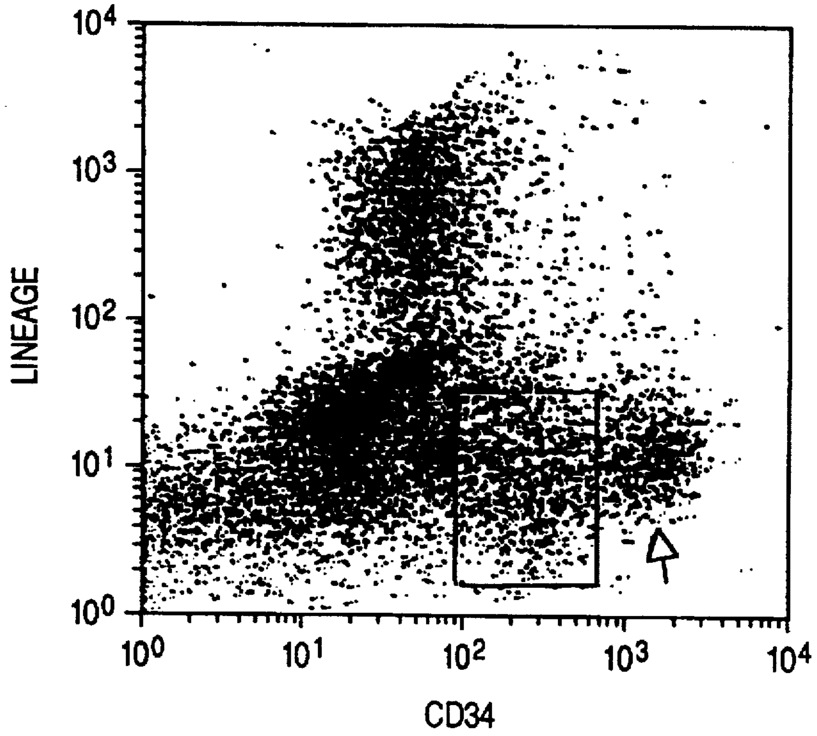

$Lin^-$ cells can be divided into some remaining $CD34^-$ and into two distinct $CD34^+$ populations. FIG. 1 shows the distribution of CD34 and lineage markers as determined by flow cytometry on an (A) isotype control and (B) on low density fetal bone marrow cells stained 20 with anti-CD34 antibody (Tuk-3) and lineage antibodies (CD14, CD15, CD16). FIG. 1(B) shows that there are two populations of $CD34^+$ cells, those expressing high levels of CD34 (arrow) and those expressing relatively low levels of CD34 (box). An average of 80% of the $CD34^+/Lin^-$ cells stained with a mean fluorescence value (MFV) 10- to 100-fold greater than that of the isotype control and are herein referred to as "$CD34^{low}$". The remaining $CD34^+/Lin^-$ cells stained with a MFV greater than 100-fold above the control, and are herein referred to as "$CD34^{hi}$".

The ability to resolve and isolate these two populations from a random sampling of tissue was determined. Table 1 shows the percentage of $CD34^+$, $CD34^-$, $CD34^{hi}$, and $CD34^{lo}$ subpopulations of low density, $Lin^-$ cells from 15 individual fetal bone marrow isolates. The percent of $CD34^+$ cells was determined by measuring all cells that stain above 99% of the isotype control (the remainder being $CD34^-$). The percentage of cells that are $CD34^{hi}$ and $CD34^{lo}$ was determined by the relative density of the CD34 antigen on the cell surface relative to the isotype control. While the percentage of low density $Lin^-$ fetal bone marrow cells that occupy the $CD34^{hi}$ and $CD34^{lo}$ compartments varies (4.6%±3.5 and 21%±6.6, respectively), the average staining intensities are highly reproducible.

TABLE 1

CD34 DISTRIBUTION ON FETAL BONE MARROW

| Tissue | CD34+ | CD34− | CD34hi | CD34lo |
|---|---|---|---|---|
| 1 | 18.7% | 81.4% | 4.1% | 14.6% |
| 2 | 24.3 | 75.7 | 4.2 | 20.1 |
| 3 | 21.9 | 78.1 | 6.3 | 15.6 |
| 4 | 23.4 | 76.6 | 2.5 | 20.9 |
| 5 | 28.5 | 71.5 | 4.0 | 24.5 |
| 6 | 20.3 | 79.7 | 4.0 | 16.3 |
| 7 | 15.2 | 84.8 | 0.9 | 14.3 |
| 8 | 32.9 | 67.1 | 3.2 | 29.7 |
| 9 | 22.1 | 77.9 | 2.4 | 19.7 |
| 10 | 25.8 | 74.2 | 1.3 | 24.5 |
| 11 | 14.8 | 85.2 | 2.1 | 12.7 |
| 11 | 25.9 | 74.1 | 4.2 | 21.7 |
| 13 | 34.4 | 65.6 | 13.9 | 20.4 |
| 14 | 49.2 | 50.8 | 10.9 | 38.3 |
| 15 | 26.4 | 73.6 | 5.2 | 21.2 |
| Average: | 25.6% | 63.8% | 4.6% | 21.0% |
| Std. Dev.: | 8.6% | 8.7% | 3.5% | 6.6% |

Table 2 shows the mean fluorescence intensity for CD34 antigen staining for nine fetal bone marrow samples as analyzed by flow cytometry, comparing the value of $CD34^{hi}$ and $CD34^{lo}$ populations to that of the isotype controls. The log of the ratio of the mean fluorescence intensity compared to the isotype control value is consistently greater than 2 for $CD34^{hi}$ and between 1 and 2 for $CD34^{lo}$ cells. Identical findings have been obtained with direct staining using a different anti-CD34 antibody (HPCA-2).

TABLE 2

CD34 ANTIGEN DENSITY MEASUREMENTS ON FETAL BONE MARROW

| | Mean Fluorescence Intensity | | | | |
|---|---|---|---|---|---|
| Tissue | Isotype Control | 34lo | 34hi | Log (34lo:Control) | Log (34hi:Control) |
| 1 | 12 | 180 | 979 | 1.18 | 1.92 |
| 2 | 5 | 121 | 818 | 1.36 | 2.19 |
| 3 | 8 | 175 | 993 | 1.35 | 2.10 |
| 4 | 6 | 83 | 789 | 1.13 | 2.11 |

TABLE 2-continued

CD34 ANTIGEN DENSITY MEASUREMENTS ON FETAL BONE MARROW

| | Mean Fluorescence Intensity | | | | |
|---|---|---|---|---|---|
| Tissue | Isotype Control | 34lo | 34hi | Log (34lo:Control) | Log (34hi:Control) |
| 5 | 4 | 152 | 583 | 1.56 | 2.14 |
| 6 | 12 | 325 | 1655 | 1.45 | 2.16 |
| 7 | 16 | 195 | 1000 | 1.10 | 1.81 |
| 8 | 6 | 157 | 979 | 1.38 | 2.18 |
| 9 | 9 | 163 | 951 | 1.28 | 2.04 |
| Average: | 9 | 172 | 972 | 1.31 | 2.07 |
| Std. Dev.: | 4 | 67 | 291 | 0.15 | 0.13 |

The reproducibility of the staining patterns were exploited in order to examine the distribution of hematopoietic progenitor activity in the $CD34^{hi}/Lin^-$ and $CD34^{lo}/Lin^-$ populations. On average, the yields of both cell populations by flow cytometric sorting ranged from 43% to 62% with typical harvests of 1 to $2\times10^6$ $CD34^{hi}$ cells and greater than $4\times10^6$ $CD34^{lo}$ per donor tissue (one set of four long bone fragments from 22–24 week fetus), representing a 25-fold enrichment and a yield of 40–60%. Sorted cells were reanalyzed immediately after sorting to measure their purity prior to assays. Sorted populations were routinely found to be very pure (>95%) with respect to contamination from $CD34^-$ or $Lin^+$ cells.

Figure 2:
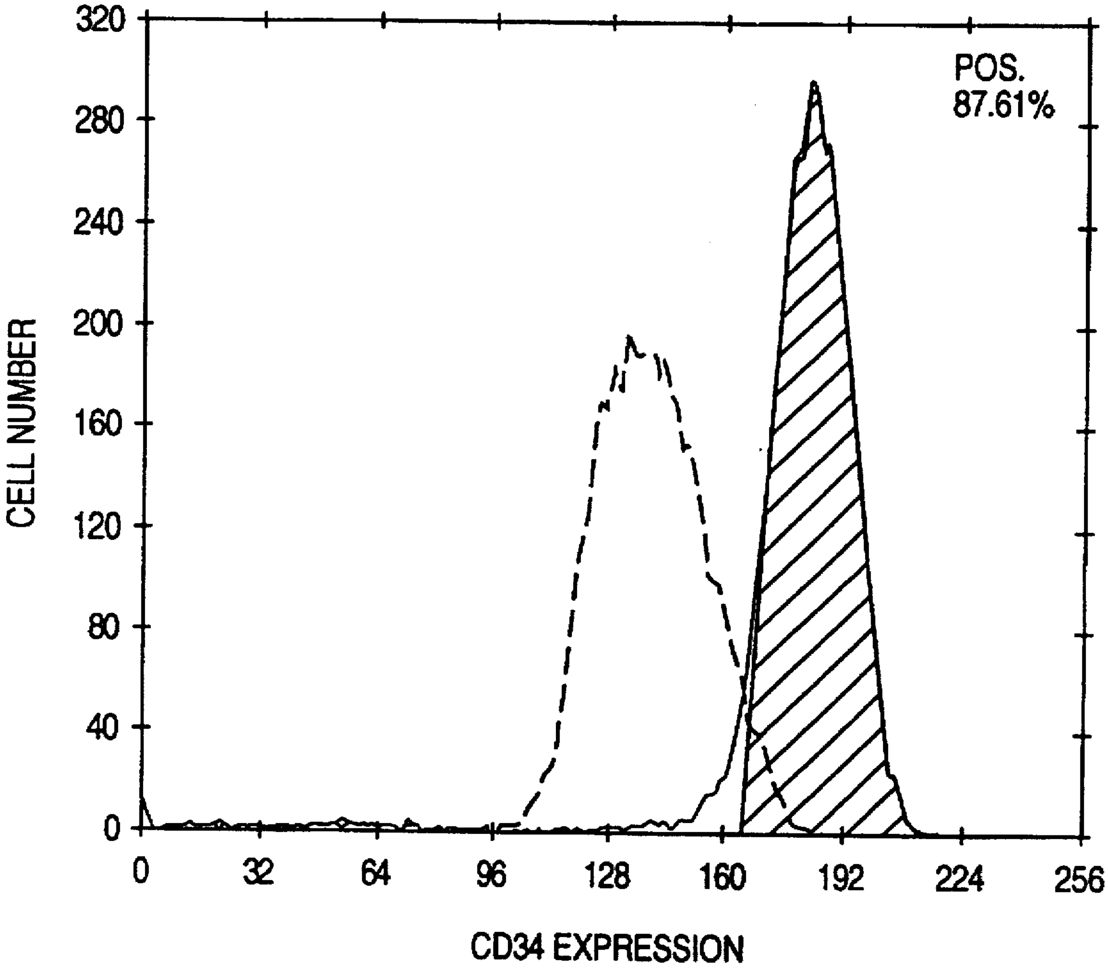
FIG. 2 shows a histogram of the CD34 fluorescence distribution of $CD34^{hi}$ and $CD34^{lo}$ sorted by flow cytometry. Sorted $CD34^{lo}$ and $CD34^{hi}$ cells were reanalyzed and the percentage overlap calculated using Multiplus Software according to the Overton subtraction procedure. The shaded portion of the curves indicates the non-overlapping portion of the two populations and hence the relative purity of the samples.
Figure 3A:
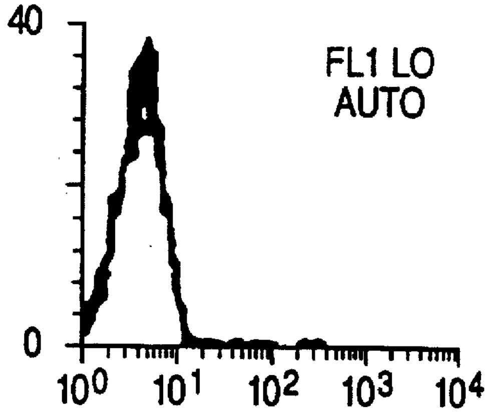
FIG. 3 shows phenotypic analysis of $CD34^{hi}$ and $CD34^{lo}$ cells. Cells sorted by flow cytometry were collected and restained with directly conjugated antibodies to other cell surface markers: CD2, CD10, CD19, CD13, CD33, CD38, HLA-DR, CD45RA, and Thy-1.
Figure 3B:
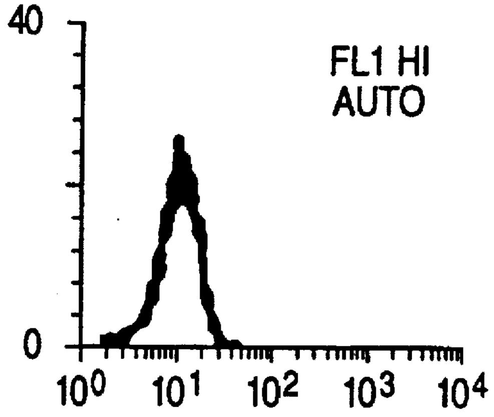
Figure 3C:
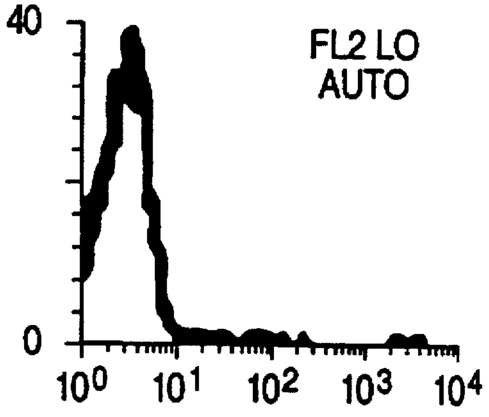
Figure 3D:
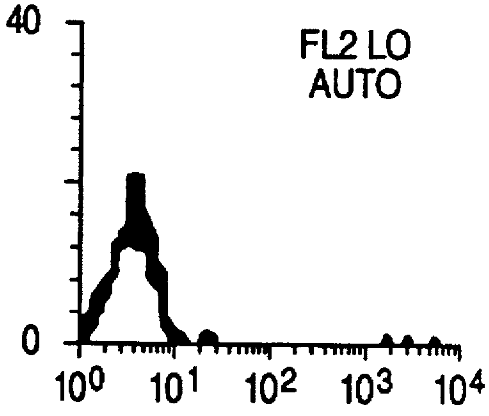
Figure 3E:
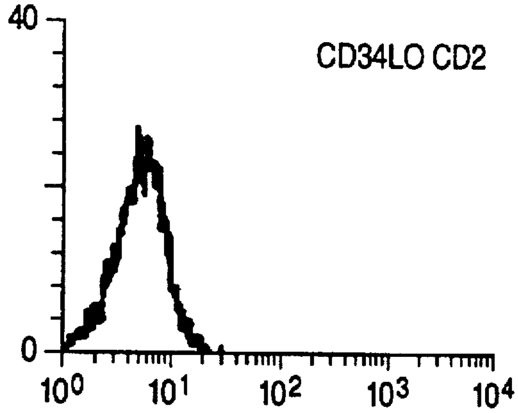
Figure 3F:
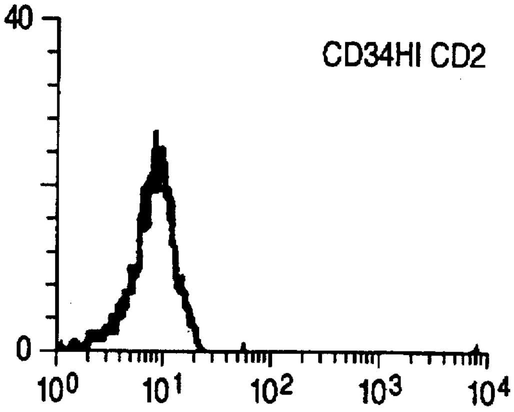
Figure 3G:
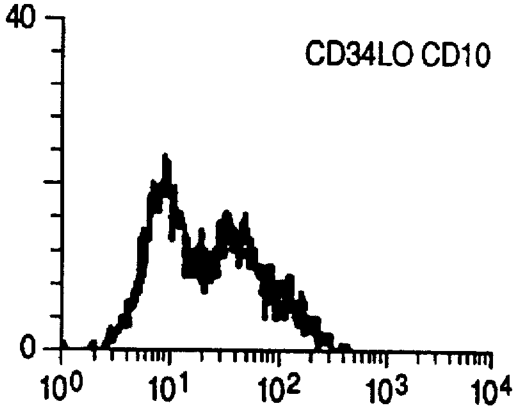
Figure 3H:
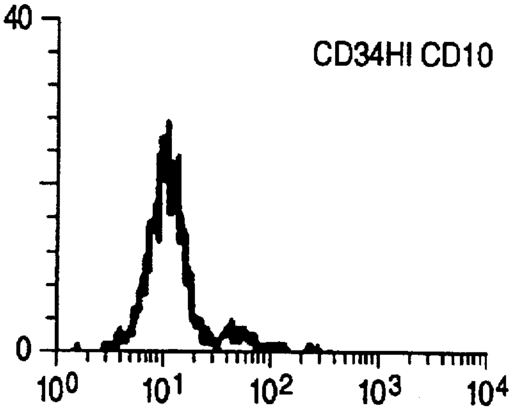
Figure 3I:
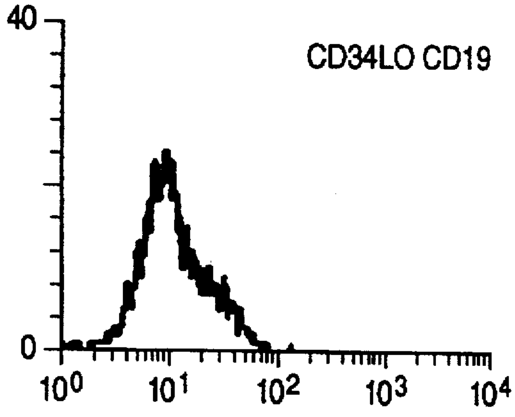
Figure 3J:
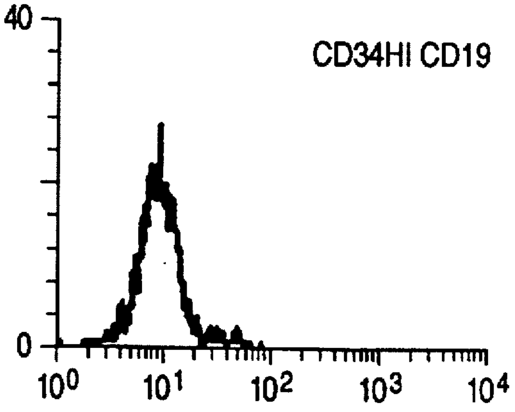
Figure 3K:
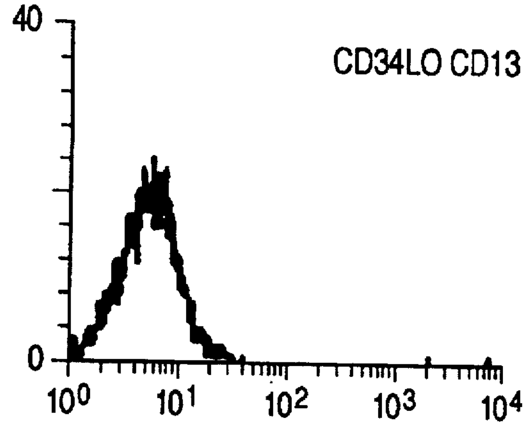
Figure 3L:
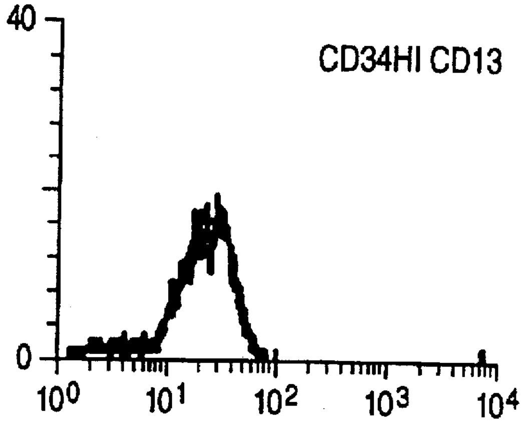
Figure 3M:
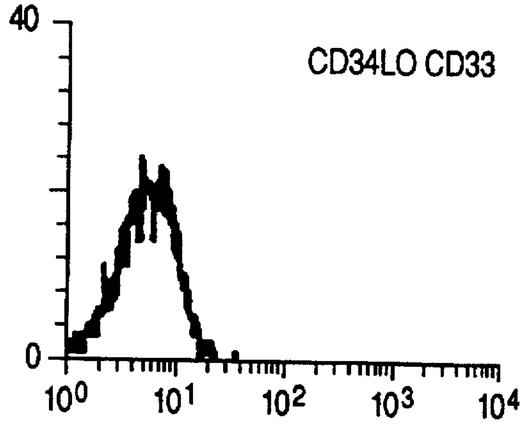
Figure 3N:
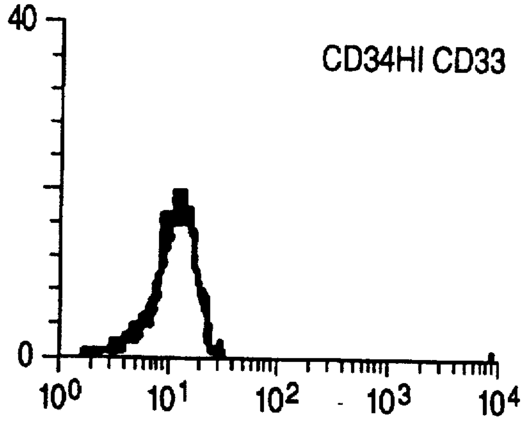
Figure 3O:
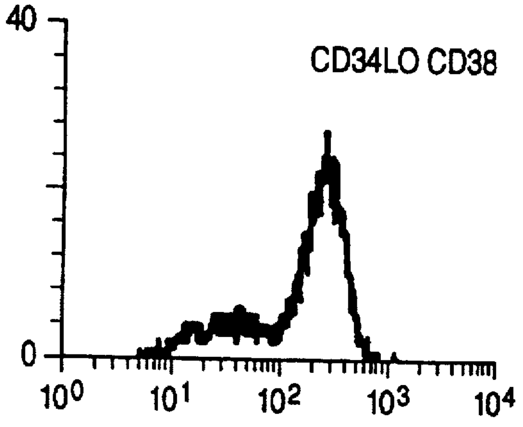
Figure 3P:
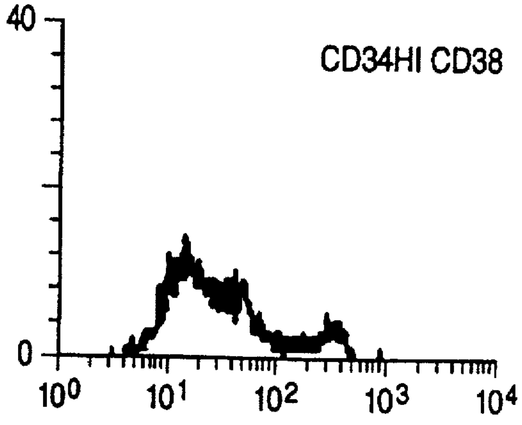
Figure 3Q:
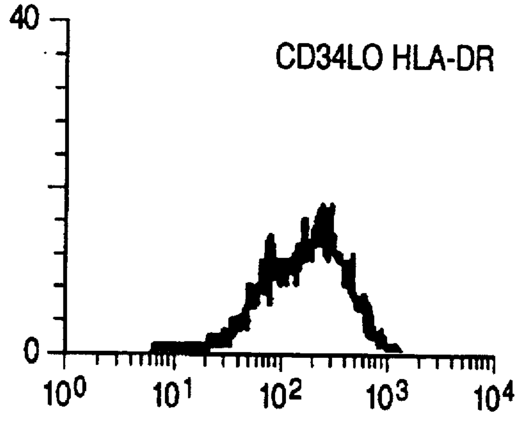
Figure 3R:
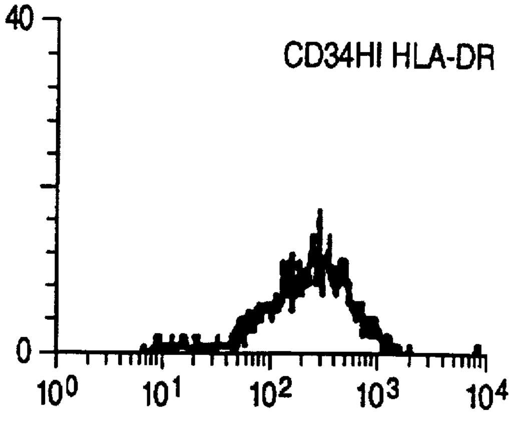
Figure 3S:
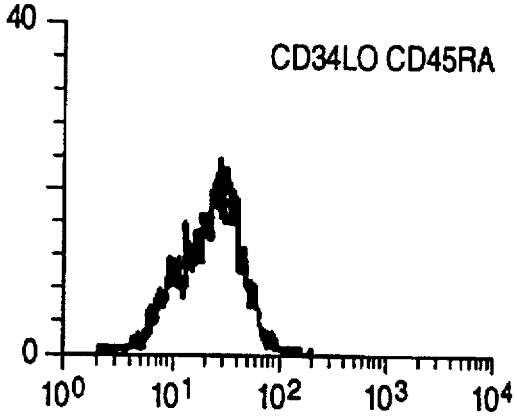
Figure 3T:
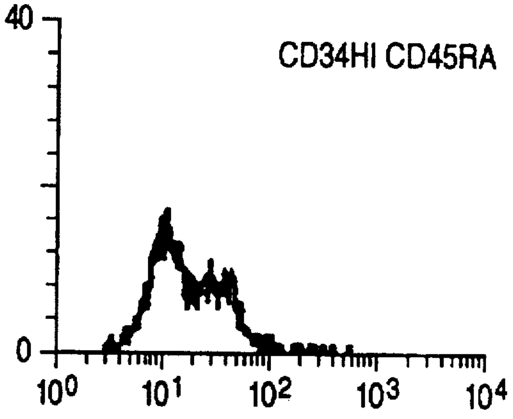
Figure 3U:
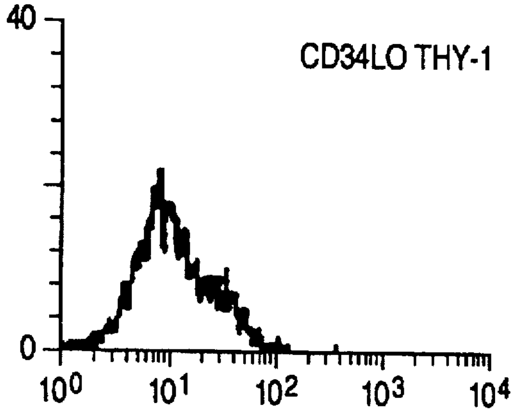
Figure 3V:
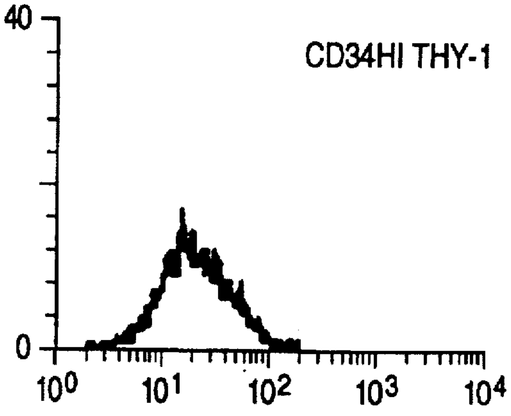

In addition, the level of contamination of $CD34^{hi}$ with $CD34^{lo}$, and vice versa, was assessed. FIG. 2 shows a histogram of the CD34 fluorescence distribution of $CD34^{hi}$ and $CD34^{lo}$ sorted by flow cytometry. Sorted $CD34^{lo}$ and $CD34^{hi}$ cells were reanalyzed and the percentage overlap calculated by the Overton subtraction procedure using Multiplus Flow Cytometric Histogram software (Phoenix Flow Systems, San Diego, Calif.). The shaded portion of the curves indicates the non-overlapping portion of the two populations and hence the relative purity of the samples. These measurements consistently gave an estimate of 85% to 95% purity; therefore 5 to 15% contamination of $CD34^{lo}$ with $CD34^{hi}$, and vice versa, was expected. Such measurements proved important for quantitative studies on populations with extremely high proliferative potential, as described below.

EXAMPLE 2

Phenotypic Analysis of Sorted $CD34^{hi}$ and $CD34^{lo}$ Populations

Bone marrow samples were stained and sorted as described above. Twenty to fifty thousand sorted cells were stained with a panel of PE- or FITC-conjugated monoclonal antibodies as described, then analyzed on a FACScan fluorescent cell analyzer (Becton Dickinson). A portion of each sorted population was incubated with the appropriate isotype control to establish the background level. The percent positive cells was determined relative to the isotype control by subtracting the background value from the experimental value.

The $CD34^{hi}$ and $CD34^{lo}$ subsets were characterized by their differential expression of a limited panel of lineage specific antigens or antigens that have been used by other groups to describe stem cells (FIG. 3). $CD34^{hi}$ cells express low levels of CD13 and CD33, are enriched for cells expressing low to intermediate levels of HLA-DR, CD38 and CD45RA, and have no detectable CD2, 10, or 19. Conversely, $CD34^{lo}$ cells express high amounts of CD38 and HLA-DR, low levels of CD19 and CD10, and no detectable CD33 or CD13. Forward and orthogonal light scatter analyses for size and granularity, respectively, reveal that both populations have low orthogonal light scatter but are fairly heterogeneous for size, although $CD34^{hi}$ cells contain a slightly larger percentage of blast cells (high forward light scatter).

The phenotypic analysis demonstrates that the $CD34^{hi}$ and $CD34^{lo}$ subsets are distinct cell populations, and that $CD34^{hi}$ cells are enriched in primitive hematopoietic cells as judged by expression of various cell surface antigens. In contrast, the $CD34^{lo}$ population appears more mature and contains a large percentage of $CD10^+CD19^+$ pre-B-cells.

EXAMPLE 3

$CD34^{hi}$ Cells Contain Virtually All Long-term in Vitro Coculture Activity The relative stem cell content of each population was determined by limiting dilution analysis and/or single cell plating of cells seeded onto pre-established murine stromal cell monolayers in 96 well plates as previously described (Baum et al. (1992) *Proc. Natl. Acad. Sci. USA* 89:2804–2808.

Briefly, $1\times10^4$ SyS-1 cells were plated in 96-well flat bottom plates one week prior to the experiment in 100 μl of a medium consisting of 50% IMDM, 50% RPMI with 10% FCS, $4\times10^{-5}$ M 2-ME, 10 mM HEPES, 100 U/ml penicillin, 100 μg/ml streptomycin, and 4 mM glutamine. Serial dilutions of sorted cells were added to stromal cells in a 100 μl volume per well.

For limit dilution analysis, 12–24 wells of each cell concentration were plated per population at four to eight cell concentrations ranging from 1000 cells per well to 33 cells per well in 200 μl final volume. For single cell deposition, 10–15 96-well plates were seeded with individual cells in 100 μl of medium and allowed to grow for one week without additional media. The following week and thereafter, media was replaced weekly by demi-depletion. Plates were visually scored from weeks 4 through 6 for the presence of tightly formed clusters of small nonrefractile cells (cobblestone areas) as previously described (Weilbaecher et al. (1991) *Blood* 78:945–952). Wells with dispersed cells or only large vacuolar cells were not counted as positive. Linear regression analysis was employed to determine the frequencies of the 4–6 week cobblestone area forming cells among sorted populations.

FIG. 4 lists the precursor frequencies for fetal bone marrow subpopulations as percent responding cells in SyS-1 coculture. Limiting dilution analysis of sorted fetal bone marrow was employed to establish the frequency of cells that form cobblestone areas between weeks four and six of culture. Some cultures were either lost to contamination or sacrificed for analysis prior to week 6 (blank spaces). The average response (AVG) and standard deviation (SD) were calculated. The number of cells containing one cobblestone area-forming cell is listed as the reciprocal of the average frequency. (1/AVG). Significant differences were observed in the growth kinetics of individual tissues, but the growth rate of all populations appeared to decline after six weeks of culture. The average frequency of responding cells calculated for the $CD34^{hi}$ subset at four weeks is 1/190 (n=6), whereas $CD34^{lo}$ cells scored with an average value of 1/3745, consistent with the readout of 5–15% contaminating $CD34^{hi}$ cells as predicted from sort purity analysis. The $CD34^+$ population gave an average frequency of 1/646. Thus, the $CD34^{hi}$ cell population had a 3.4- to 4-fold increase in precursor frequency over the $CD34^+$ population, which approaches a quantitative recovery of all of the activity in the $CD34^{hi}$ compartment. It was also confirmed that the $CD34^-$ and $Lin^+$ populations had no activity in this assay.

These results demonstrate that $CD34^{hi}$ cells contain virtually all the long-term coculture activity contained in fetal bone marrow.

EXAMPLE 4

In Vitro Differentiation Along Multiple Lineages

The nature of the progeny of cultured cells was directly examined by phenotypic analysis. Positive wells from limit dilution cultures were stained by two-color immunofluorescence using fluorescently labeled antibodies specific for B cells (CD19) and myeloid cells (CD33), then analyzed by flow cytometry.

Figure 5A:
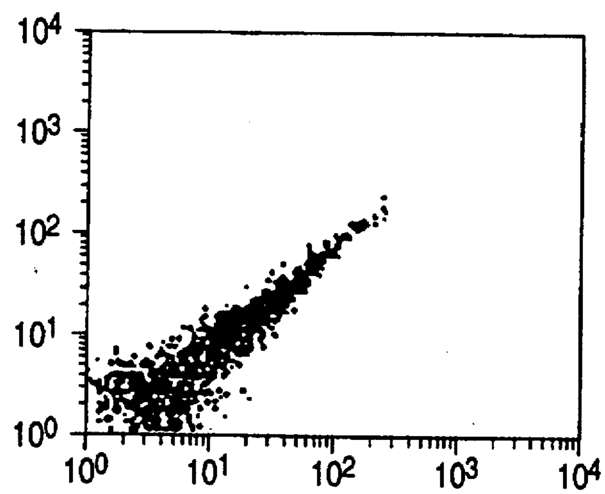
FIG. 5 shows phenotypic analysis of bulk cultures of $CD34^{hi}$ cells. $CD34^{hi}$ cells were cultured on a stromal cell layer for six weeks, then the entire culture was harvested and stained with either the appropriate isotype matched antibodies (A), anti-CD10 and anti-CD19 (B), or anti-CD15 and anti-CD33 (C). Stromal cells and dead cells were excluded by light scatter and dye exclusion gating.
Figure 5B:
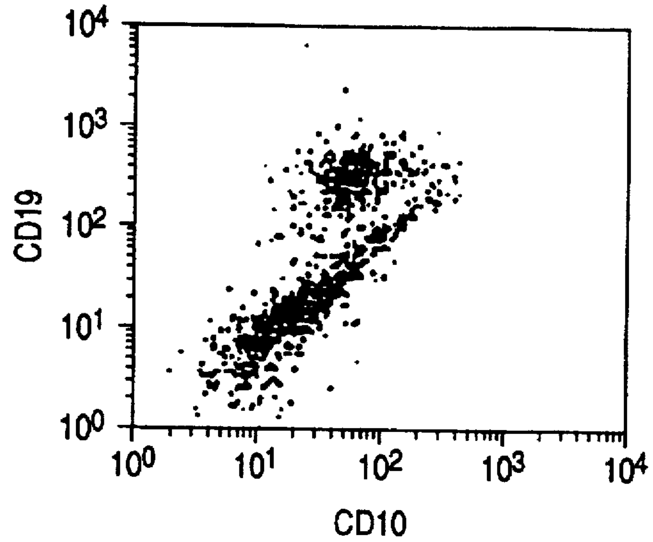
Figure 5C:
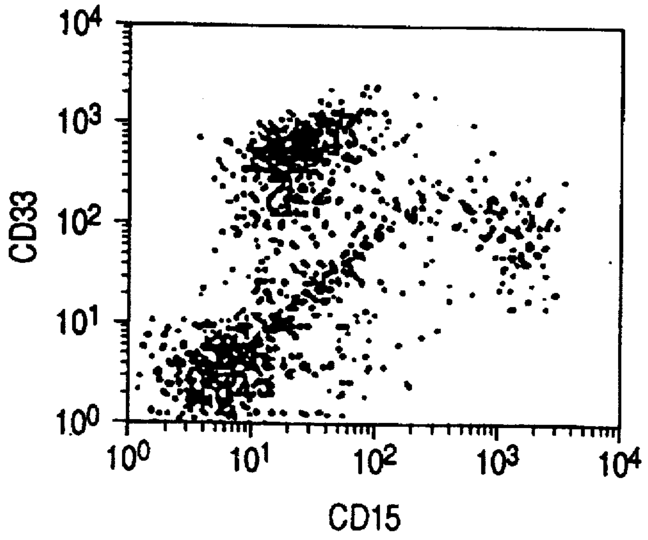

FIG. 5 shows phenotypic analyses of bulk cultures of $CD34^{hi}$ cells. $CD34^{hi}$ cells were cultured on a stromal cell layer for six weeks, then the entire culture was harvested and stained with either the appropriate isotype matched antibodies (A), antibodies to the B cell progenitor surface markers CD19 and CD10 (B), or antibodies to myeloid progenitor cell markers CD15 and CD33 (C). Stromal cells and dead cells were excluded by light scatter and dye exclusion gating. As shown in FIG. 5, approximately 80% of the wells analyzed showed populations expressing both B and myeloid cell markers. A fraction (approximately 1%) of the cells in cultures initiated with $CD34^{hi}$ cells maintained their initial $CD34^{hi}$ phenotype and could be isolated again and used to reinitiate long-term cultures. These findings confirm that cells that are capable of initiating long term cultures also possess the ability to generate cells of disparate lineages. The culture system described above is also shown to be capable of maintaining early progenitor cells for up to six weeks of culture.

EXAMPLE 5

Long-term Hematopoietic Reconstitution of Human Bones Implanted into SCID Mice Human fetal bone fragments implanted in the immunodeficient SCID mice can sustain active human hematopoiesis in vivo for as long as 20 weeks (Kyoizumi et al. (1992) *Blood* 79:1704–1711). The long term persistence of multiple lineages indicates that this in vivo system provides the microenvironment necessary to sustain long-term differentiation of human hematopoietic stem cells. Animal studies as well as clinical transplantation in humans have shown that stem cells can engraft across allogeneic barriers (McCune et al. *Science* (1988) 241:1632–1639). The SCID-hu bone model was therefore adapted to receive and engraft with allogeneic human hematopoietic stem cells.

For the SCID-hu bone assay, female C.B-17 scid/scid (SCID) mice were bred under sterile conditions and protected by antibiotic treatment in drinking water (sulfamethoxazole and trimethoprim, 400 and 80 mg/kg mouse/wk, respectively). Mice between 6 to 8 weeks of age were used. Human fetal long bones obtained as mentioned above were split lengthwise and transversely cut in half to yield 4 bone fragments per long bone. These fragments were immediately implanted subcutaneously into the SCID mice mammary fat pads. Usually two bone pieces are engrafted into each mouse. An anesthetic combination of methoxyflurane vapors with an intramuscular injection of ketamine hydrochloride (50 mg/kg) and xylazine hydrochloride (25 mg/kg) was used to perform all operative procedures. A sample of the fetal tissue was stained for HLA markers. Transplanted SCID mice (SCID-hu bone mice) were used 5 to 12 weeks later as recipients of the sorted populations after a second HLA immunophenotyping showed mismatch between the implanted fetal bone fragments and the sorted cells. Immediately prior to injection, SCID-hu bone mice were irradiated with 350 rads in a single dose dispensed with a 1500 Ci $^{137}Cs$ source using a 30% attenuation shielding (J. L. Sheperd & Assoc., San Francisco, Calif.). Experiments were performed to determine that SCID mice could tolerate a dose of total body irradiation up to 400 rads, considerably below the level that normal healthy mice can tolerate. At doses of 350 to 400 rads, engraftment of donor-derived cells reached a level of greater than 50%, usually 80%. Sorted cells were then injected directly into the bone using a Hamilton syringe in a 10 μl volume. SCID-hu bone mice were kept for 5 to 9 weeks, then sacrificed by cervical dislocation. Human bones were removed and adherent tissues dissected away. The bones were split open in order to flush the marrow cavity with SB. Collected cells were spun down and the pellet was resuspended for 10 minutes into a red blood cell lysing solution (Kyoizumi et al. (1992) to lyse red blood cells. Cells were washed twice and counted before being stained by two-color immunofluorescence with directly labeled antibodies against HLA in combination with anti-CD19, -CD20, -CD33, -CD14, and -CD34. Grafts with low numbers of cells may be pooled to facilitate staining. FITC- and PE-conjugated irrelevant mouse immunoglobulins were used as negative controls. Analysis was performed on a FacScan fluorescence activated cell scanner (Becton Dickinson).

After the SCID mice had been implanted with human bone fragments, they were allowed to recover for a minimum of 5 weeks. They were then subjected to total body irradiation to deplete the implanted bones of hematopoietic cells. Immediately following irradiation, 1.5 to $5\times10^4$ sorted fetal $CD34^{hi}$ and $CD34^{lo}$ cells were directly injected into the bone cavity. Cells were sorted against an extended Lin panel which in addition to CD14, CD15, and CD16 included CD2, CD20, and glycophorin in order to ensure complete depletion of mature committed cells or cells with a potentially detrimental effect in such an allogeneic setting. It had been ascertained that these mature CD2, CD20, and glycophorin $A^+$ cells were exclusively contained in the $CD34^-$ compartment, so that their removal did not compromise the composition of the $CD34^{hi}$ and $CD34^{lo}$ subsets. Sort purities were routinely greater than 95%.

Animals were sacrificed five to nine weeks later, and the human bones retrieved and analyzed using two-color immunofluorescence. A combination of an antibody against class I MHC molecule monomorphic determinants (W6-32) and CD45 was used to calculate the percentage of human cells in each graft. A combination an antibody specific for an HLA polymorphic determinant of donor cells and of W6-32 or of lineage specific markers was used to calculate the donor reconstitution in the grafts.

Table 3 presents the results of the reconstitution of SCID-hu bones by CD3.4 sets in three distinct experiments in which the human bones were injected with 1.5 to $5\times10^4$ fetal bone marrow CD34 subsets or noninjected. Grafts were retrieved 5 to 9 weeks after injection, cells counted and stained for the presence of $CD45^+$/HLA class $I^+$ human and donor cells. The cell numbers retrieved from grafts varied, but there were no significant differences in the overall cellularity (i.e., cell number) of the bones whether they were injected with $CD34^{hi}/Lin^-$ or $CD34^{lo}/Lin^-$ fetal bone marrow cells or uninjected. However, bones reconstituted with $CD34^{hi}$ cells contained a more consistent percentage of human cells (91±5%) with an average of 67±27% (ranging from 23% to 99%) donor derived cells (n=14), whereas bones injected with the $CD34^{lo}$ subset as well as non-injected bones contained no detectable donor cells and had an average of 68±38% and 72±34% host derived human cells, respectively. The remainder of the cells were of mouse origin.

TABLE 3

RECONSTITUTION OF SCID-Hu BONES BY CD34 SUBSETS

| | # cells injected (× $10^4$) | # grafts | # cells recovered (× $10^5$) | % cells in grafts human | donor |
|---|---|---|---|---|---|
| Control | 0 | 5 | 2.6 ± 2.4 | 72 ± 34 | 0 |
| CD34lo | 1.5–5 | 14 | 2.2 ± 3.2 | 68 ± 38 | 0 |
| CD34hi | 1.5–5 | 14 | 2.9 ± 4.0 | 91 ± 5 | 67 ± 27 |

Figure 6A:
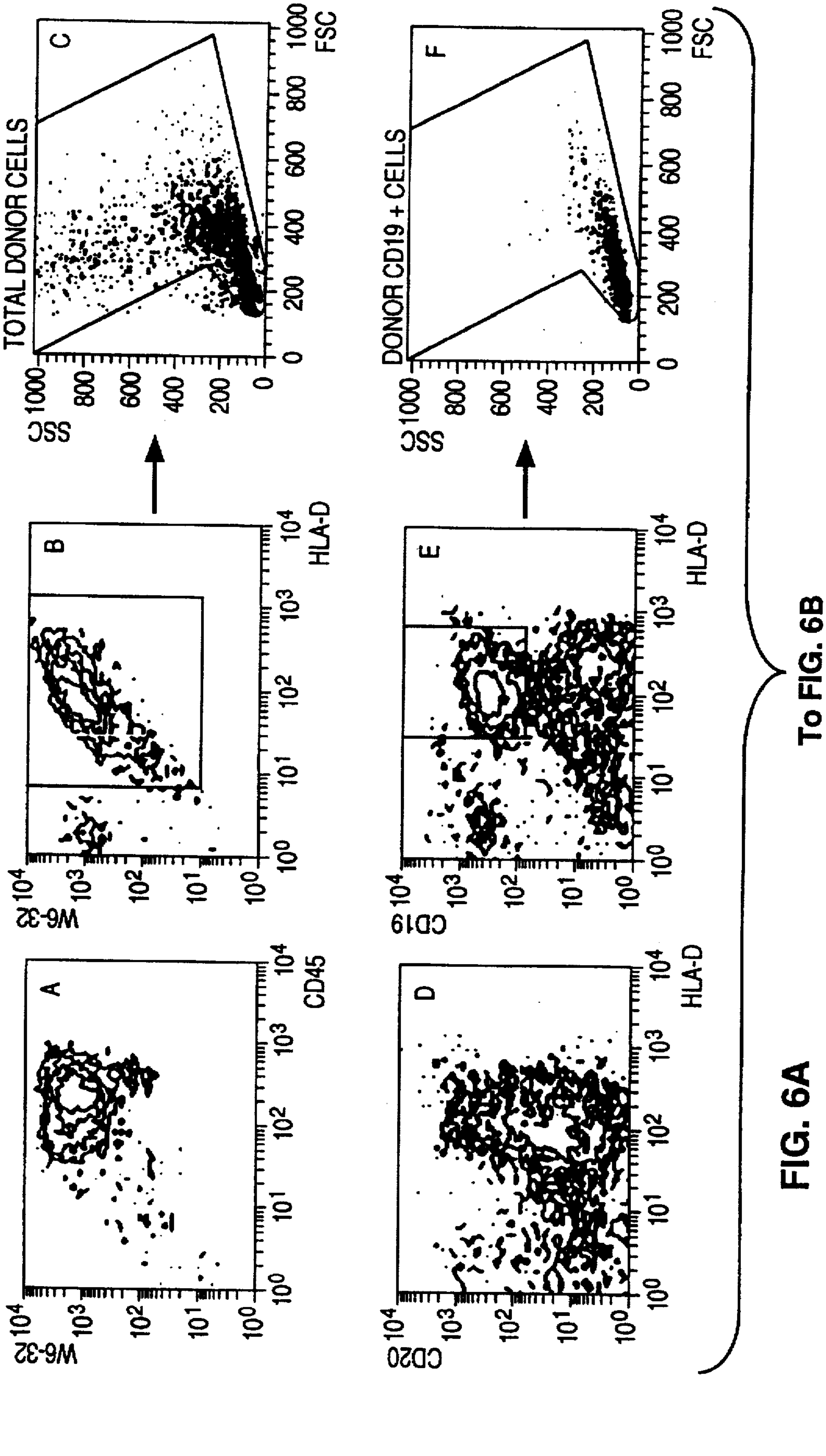
FIG. 6 shows FACS analyses of cells from a representative SCID-hu bone graft injected with $5\times10^4$ allogeneic $CD34^{hi}$ fetal bone marrow cells and retrieved after nine weeks. Cells were stained with CD45 and W6-32 or donor HLA (HLA-D) and W6-32 antibodies, (top left panels). Gating on the donor population revealed a heterogeneous distribution of bone marrow cells (upper right panel). B-cells were identifiable by expression of CD19 and CD20. Gating on $CD20^+$ donor cells showed forward (FSC) and side scatter (SSC) characteristics of B-cells (middle right panel). $CD33^+$ donor cells were observed in the expected myeloid region of bone marrow cells (bottom left panel). $CD14^+$ monocytes had characteristic size and granularity features (lower middle right panel). A population of $CD34^+$ donor cells was identifiable (14% of total sample); the specificity of staining was controlled by lack of immunoreactivity with irrelevant antibodies (bottom right panel).
Figure 6B:
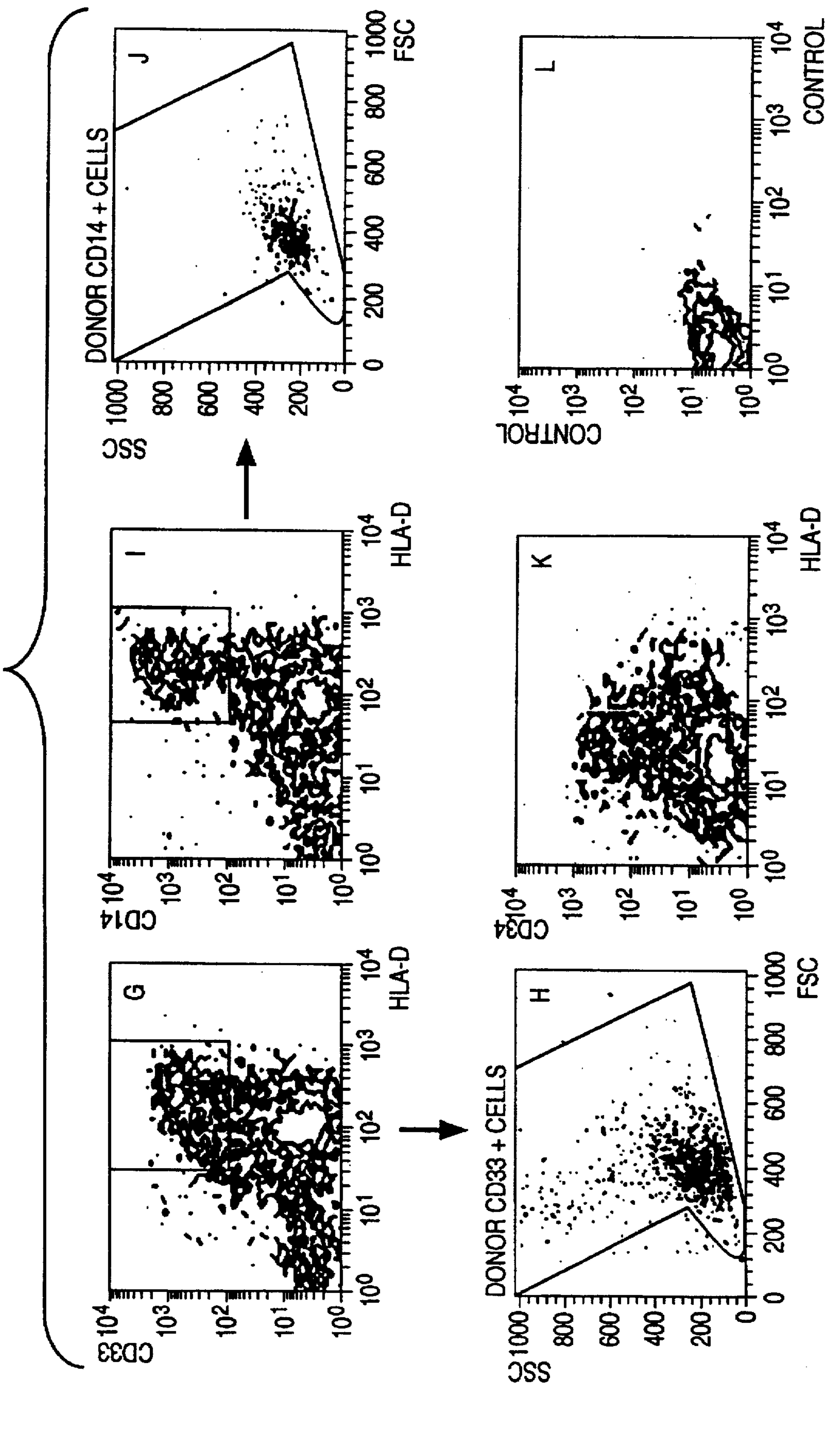

Bone grafts were further analyzed for phenotypic composition. FIG. 6 shows the results from staining a representative SCID-Hu bone graft reconstituted with allogeneic $CD34^{hi}$ fetal bone marrow cells and retrieved after nine weeks. 96% of the cells coexpressed CD45 and W6-32, indicating they were human cells. 91% of the cells coexpressed the anti-polymorphic HLA of the donor in combination with W6-32, indicating that they were donor derived (top left panels). Gating on the donor population revealed a heterogeneous distribution of bone marrow cells, typically indicative of the presence of multiple lineages (upper right panel). B-cells were clearly identifiable by expression of CD19 and CD20. Donor derived $CD19^+$ represented 57% of the total sample and $CD20^+$ represented 42%. Gating on $CD20^+$ donor cells showed forward (FSC) and side scatter (SSC) characteristics of B-cells (middle right panel). $CD33^+$ donor cells were also found and were observed to distribute in the expected myeloid region of bone marrow cells (bottom left panel). Also, $CD14^+$ monocytes could be identified with characteristic size and granularity features (lower middle right panel). Donor-derived $CD33^+$ represented 30% of total sample and $CD14^+$ represented 11%. A population of $CD34^+$ donor cells was identifiable (14% of total sample); the specificity of staining was controlled by lack of immunoreactivity with irrelevant antibodies (bottom right panel).

In sharp contrast, $CD34^{lo}$ cells never engrafted, so no donor progeny could be identified and the phenotypic profile of the grafts was identical to that of noninjected controls, showing only the recovery of host hematopoiesis. Fetal bone marrow $CD34^-$ cells were tested and likewise showed no engraftment. Because of the initial sort purities and because donor-derived myeloid cells were retrieved after nine weeks, these results argue against maintenance or expansion of mature cells but strongly demonstrates multilineage differentiation from the $CD34^{hi}$ stem cell-containing population. These results demonstrate the long term potential of $CD34^{hi}$ cells and closely parallel the in vitro observations discussed in Example 4, confirming that all the B and myelopoietic potential associated with fetal bone marrow is found solely in the $CD34^{hi}$ cell compartment.

EXAMPLE 4

Long-term T-cell Reconstruction Potential of CD34 Subsets

Human fetal $CD34^+$ cells can reconstitute a depleted allogeneic thymus cultured in vitro or implanted into SCID mice and generate donor-derived thymocytes (Galy et al. (1993) *J. Exp. Med.* 178:391–401; Peault et al. (1991) *J. Exp. Med.* 176:1283–1286). In contrast to the in vitro culture assays, the SCID mouse model allows maintenance of donor-derived T-cells for as long as 4.5 months.

A three-color immunostaining procedure was used to stain thymocytes recovered from thymic grafts to assess the quality of donor-derived thymopoiesis by examining the coordinated expression of CD1a, CD3, CD4 and CD8 molecules. Thoroughly depleted thymic grafts were reconstituted with CD34 subsets from allogeneic fetal bone marrow and analyzed after 6 to 14.5 weeks.

For the SCID-hu thymus assay, as reported earlier (Peault et al. (1991), 19–22 week-old fetal thymuses were dissected and fragments containing two to four intact lobules were placed on nitrocellulose filters (0.8 μm, Costar Corp., Cambridge, Mass.) on top of gelatin rafts (Gelfoam, Upjohn, Kalamazoo, Mich.) in RPMI medium containing 10% FCS and P/S. A sample of thymocytes was taken for HLA immunophenotyping of the recipient thymus. After seven days of incubation at 25° C. and 5% $CO_2$, fragments were irradiated with 250 rads given without attenuation in a single dose on a $^{137}Cs$ source irradiator (J. L. Shepherd & Assoc.). Fragments were washed and immediately microinjected with the HLA mismatched sorted cell populations in a 1 μl volume using an oil-filled microinjector (Narishige, Japan) and 1 mm diameter glass micropipets (World Precision Instruments, Sarasota, Fla.). Fragments were placed back on the filters and incubated at 37° C. with 5% $CO_2$ overnight, then inserted under the kidney capsule of anesthetized 6 to 8 week-old SCID mice. Mice were sacrificed by cervical dislocation at various times after the transplantation, and the thymus grafts were recovered, reduced to a cellular suspension, and subjected to a three-color immunofluorescence analysis on the FACScan, using mAbs directly labelled with FITC, PE and TR. Grafts with low numbers of cells may be pooled to facilitate staining. Samples were analyzed on the FACScan to determine the proportion of human and donor-derived cells (combination of HLA of donor, anti-class I monomorphic and CD45) and the quality of the thymopoiesis (combination of HLA of donor and CD1a plus CD3, or CD4 plus CD8).

Figure 7:
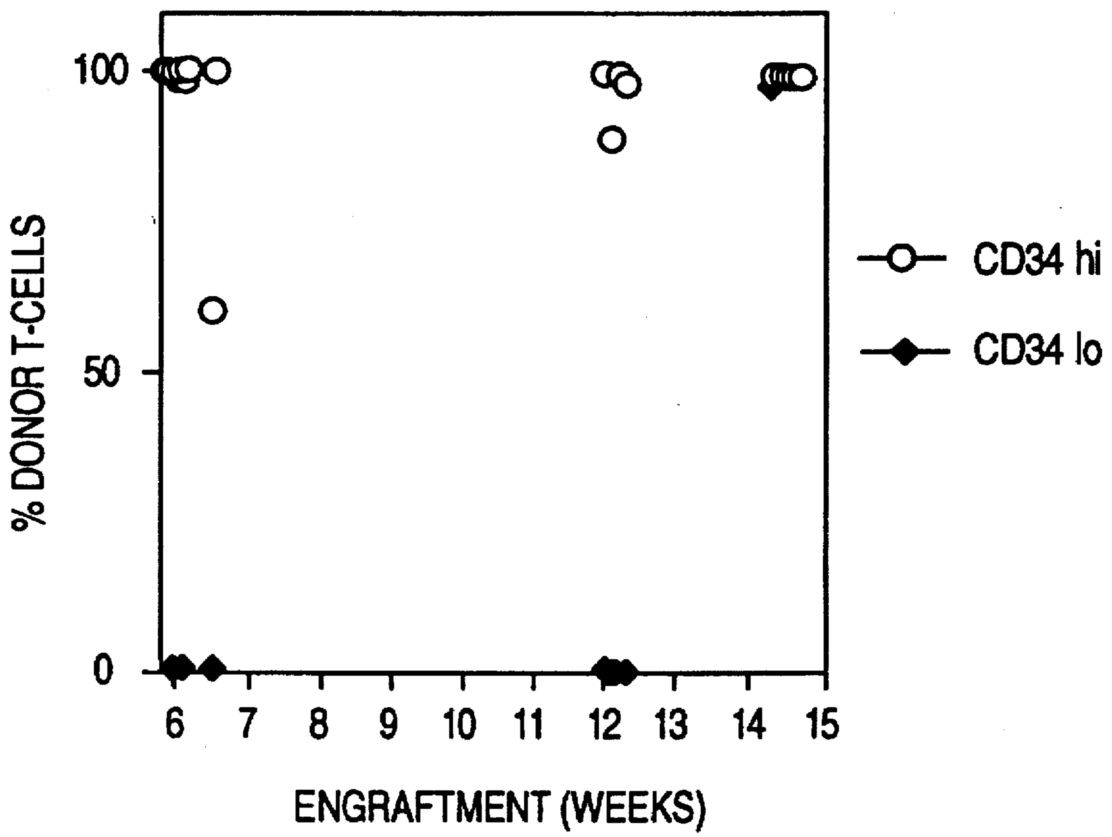
FIG. 7 shows engraftment of CD34 subsets in the SCID-Hu thymus assay. Depleted thymic fragments were injected with $1\times10^4$ fetal bone marrow $CD34^{hi}$ or $CD34^{lo}$ cells and implanted into SCID mice. Thymic grafts were retrieved after 6 to 14.5 weeks and analyzed for the combined expression of CD45, W6-32 and HLA-D. These cells also express T-cell specific markers, either CD1, CD3, CD4, or CD8.
Figure 8A:
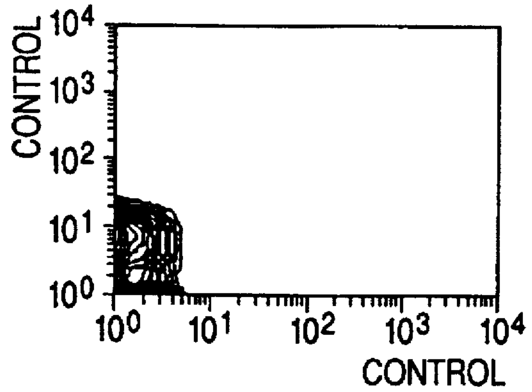
FIG. 8 shows FACS analyses of two representative SCID-Hu thymus grafts, one injected with $CD34^{hi}$ cells (right panels, top to bottom) and the other unsuccessfully reconstituted with $CD34^{lo}$ cells (left panels—top to bottom).
Figure 8B:
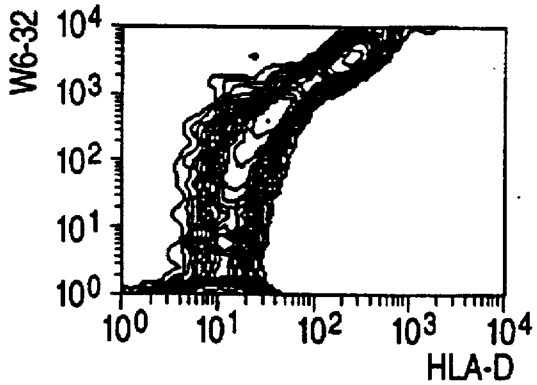
Figure 8C:
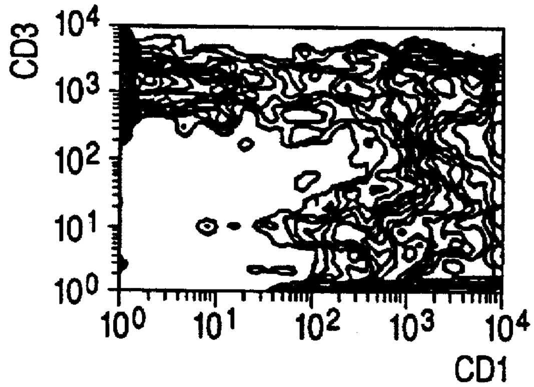
Figure 8D:
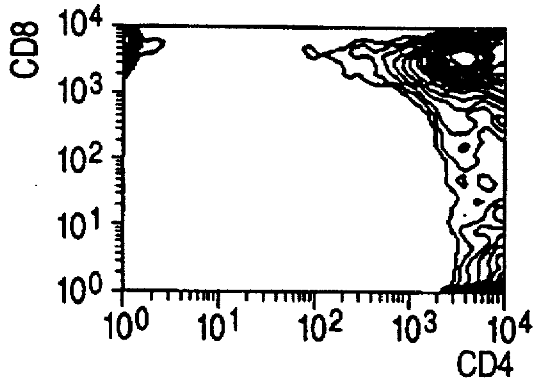
Figure 8E:
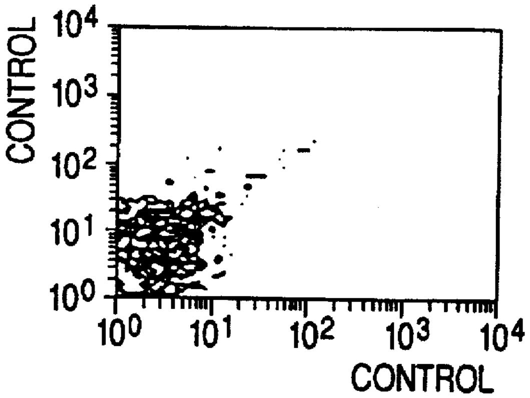
Figure 8F:
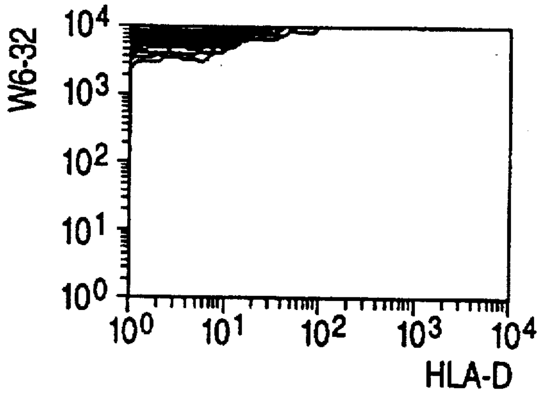
Figure 8G:
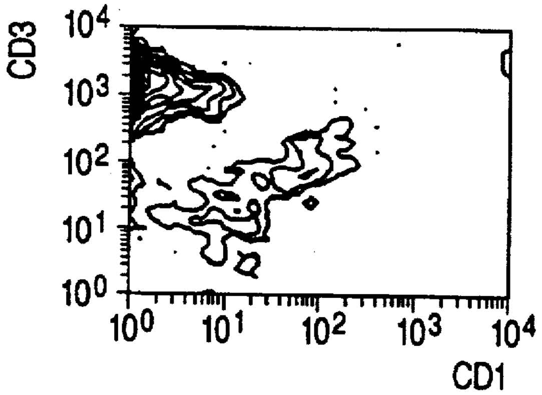
Figure 8H:
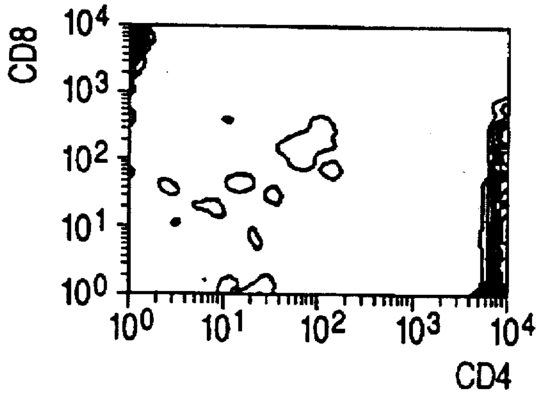

In five different experiments the vast majority (81%, n=32) of the grafts injected with $CD34^{hi}$ cells maintained their high percentage of donor T-cells even after 14.5 weeks, whereas grafts injected with $CD34^{lo}$ were rarely recovered (one graft at week 14.5) much like the control non-injected thymi. As shown in FIG. 7, those injected with $CD34^{hi}$ cells consistently contained donor-derived cells arising from thymopoiesis, with percentages of thymic reconstitution ranging from 60 to 100%.

Further phenotypic analysis (FIG. 8) showed that the T-cell progeny of $CD34^{hi}$ fetal bone marrow cells closely resemble those of normal fetal thymocytes, based on the high expression of CD1a, graded levels of CD3 staining, and co-expression of CD4 and CD8 on the majority of thymocytes, although there were a small number of single positive CD4 or CD8 cells. The graft injected with $CD34^{hi}$ cells showed complete reconstitution with thymocytes coexpressing HLA class I monomorphic and specific determinants of the donor. In contrast, the graft injected with the $CD34^{lo}$ subset was not reconstituted with any donor cells, and all thymocytes recovered were of host origin, having matured to express very high amounts of class I antigens and of CD3, no CD1; there were no cells positive for both CD4 and CD8. In sharp contrast, only one of nine recovered grafts injected with $CD34^{lo}$ cells contained donor cells.

Furthermore, this graft contained only donor-derived mature thymocytes. After 12 weeks, host thymocytes had completely differentiated into MHC class I bright cells with high levels of CD3 without CD1 or co-expression of CD4 and CD8.

Therefore, only $CD34^{hi}$ fetal bone marrow cells were capable of engrafting an allogeneic thymus and generating T-cells for sustained periods of time. It was also confirmed that $CD34^-$ fetal bone marrow cells were devoid of pre-T-cell activity. Taken together, these data clearly show that the capacity to generate T, B, and myeloid cells is exclusively restricted to the $CD34^{hi}$ compartment of the fetal bone marrow.

The hallmark of a very early hematopoietic progenitor cell (or stem cell) is the ability to differentiate into multipotent progenitors and generate long term hematopoiesis in immunocompromised hosts. Cocultivation of primitive progenitor cell populations on marrow-derived stromal cells has been shown to maintain active hematopoiesis for extended periods of time (8–12 weeks). Long term stromal coculture assays have been extensively used to determine the hematopoietic stem cell content of candidate populations. In humans, the myelo-erythroid potential is generally assayed and direct evidence is often lacking to correlate this activity with primitiveness, particularly in the lymphoid lineage.

The present disclosure, however, demonstrates the in vitro generation of $CD19^+$ B cells from most tissues tested for up to 8 weeks of culture. Myelopoiesis was evident in the same cultures with expression of CD33. Cells found after 6 weeks of culture likely arose from primitive hematopoietic stem cells for a number of reasons. First, there was no detectable CD10 or CD19 on the surface of $CD34^{hi}$ cells, ruling out the possibility that early B cell progenitors contaminating the starting population had been maintained. Second, the culture conditions used did not support the maintenance of the CD10 or CD19 positive $CD34^{lo}$ population over the 6 weeks of culture; thus the expansion of contaminating lineage-committed progenitors is unlikely. Third, experiments designed to test clonogenic potential of the $CD34^{hi}$ population showed B and myeloid cells in up to 5% of wells seeded with single cells. Also noteworthy was the maintenance of the $CD34^{hi}/Lin^-$ phenotype in 6 week cultures, which have been used to reinitiate long term cultures. Finally, long term B and myelopoiesis were confirmed using the SCID-hu bone model, and a perfect correlation was confirmed between these assays and the capacity to make T-cells in the SCID-hu thymus assay.

Together, these data indicate that maintenance of long-term cobblestone areas in the above-described assays correlates with the presence of a very primitive and multipotent hematopoietic progenitor. Differentiation of candidate human stem cell populations into the T-cell lineage has been infrequently reported. Using the SCID-hu mouse model, long term T lymphopoiesis was examined, and it was particularly instructive to observe the generation of immature $CD1a^+$, double positive thymocytes for long periods of time such as 12–15 weeks, since this observation undoubtedly indicates the presence of a very immature pre-thymic progenitor. Indeed, a thymic piece implanted alone engrafts very poorly and does not generate immature thymocytes ($CD1^+$) past 6 weeks, unless a source of progenitors is added in the form of a fetal liver fragment or microinjected stem cells. Thus, the thymus itself does not seem to contain stem cells or rapidly exhausts the small number of stem cells that it may contain.

Numerous injections of purified $CD34^+$ populations that were completely HLA-mismatched with the recipient thymus or bone have been performed and have not met with allogeneic barriers leading to graft failure. This indicates that the in vivo assays disclosed herein are well suited to the study of human allogeneic stem cell transplantation, and reinforces the usefulness of these assays as pre-clinical models (see Kyoizumi et al. (1993) *Blood* 81:1479–1488).

Limiting dilution analysis of $CD34^{hi}$ cells on SyS-1 stroma revealed that the stem cell activity was contained in about 0.5–1% of $CD34^{hi}$ cells, which represents a 100-fold increase over whole bone marrow and a 3–5-fold increase over $CD34^+$ cells.

All publications and patent applications cited in this specification are incorporated herein by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for obtaining a cell population enriched in hematopoietic stem cells comprising the steps of:

combining a mixed population of fetal or neonatal cells comprising hematopoietic stem cells with fluorescently labeled antibodies which bind specifically to CD34;

removing unbound antibodies; and selecting cells which have mean fluorescence values for CD34 surface antigen of at least two logs greater than that of isotype controls.

2. The method according to claim 1 wherein the cells are human cells.

3. The method according to claim 2 wherein the cells are fetal cells.

4. The method according to claim 3 wherein the cells are bone marrow, liver, or blood cells.

5. The method according to claim 2 wherein the cells are cord blood cells.

6. A composition obtained by a process comprising the steps of:

combining a mixed population of fetal or neonatal cells with fluorescently labeled antibodies which bind specifically to CD34;

removing unbound antibodies; and selecting cells which have mean fluorescence values for CD34 surface antigen of at least two logs greater than that of isotype controls.

7. A method of reconstituting hematopoiesis in an immunocompromised animal, the method comprising introducing into the animal a composition according to claim 8.

8. A method for evaluating a sample for the presence of a biological modifier capable of affecting a biological response of a hematopoietic stem cell, the method comprising the steps of:

plating a test cell obtained according to the method of claim 1 in an appropriate culture system along with the sample;

plating a control cell obtained according to the method of claim 1 in an appropriate culture system without the sample; and comparing the biological response of the test and control cells.

9. The method according to claim 1 wherein the cell obtained from claim 1 has been further selected for lack of expression of at least one lineage specific marker.

10. The method according to claim 9 wherein the lineage specific marker is at least one of CD14 and CD15.

11. A method for measuring the stem cell content in a sample comprising the steps of:

(a) combining a mixed population of fetal or neonatal cells comprising hematopoietic stem cells with fluorescently labeled antibodies which bind specifically to CD34;

(b) removing unbound antibodies;

(c) selecting cells which have mean fluorescence values for CD34 surface antigen of at least two logs greater than that of isotype controls; and (d) quantifying the amount of selected cells resulting from step (c) relative to the quantity of cells used in step (a).

12. The method according to claim 11 further comprising the step of selecting the cells for lack of expression of at least one lineage specific marker.

13. The method according to claim 12 wherein the lineage specific marker is at least one of CD14 and CD15.

14. A method of modifying a stem cell, the method comprising transfecting a stem cell obtained according to the method of claim 1 with a nucleic acid capable of expressing in the transfected cell or its progeny either a polypeptide or the nucleic acid, thereby modifying the stem cell.

15. The method of claim 14, wherein the nucleic acid encodes a nucleic acid or a polypeptide that is missing or defective in the cell.

16. A stem cell obtained according to the method of claim 14.

17. A stem cell obtained according to the method of claim 15.

* * * * *

UNITED STATES PATENT AND TRADEMARK OFFICE

CERTIFICATE OF CORRECTION

PATENT NO. : 5,681,559

DATED : October 28, 1997

INVENTOR(S) : David DiGiusto and Anne H.M. Galy

It is certified that error appears in the above-indentified patent and that said Letters Patent is hereby corrected as shown below:

Column 2, line 8, "Brandt" should be --Hoffman--
line 11, after "Sci." insert --USA--

Column 5, line 17, "Brandt" should be --Hoffman--
line 17, after "(1988)" insert --*J. Clinical Investigation* 82:1017-1027--
line 19, after "(1992)" insert --*J. Exp. Med.* 175:1501-1509--

Column 10, line 57, "Me" should be --ME--

Column 11, line 16, "solution+2%" should be --solution + 2%--
line 17, "i" should be --1--
line 61, delete "20"

Column 12, Table 1, column 1, "11" (second occurrence) should be --12--

UNITED STATES PATENT AND TRADEMARK OFFICE

CERTIFICATE OF CORRECTION

PATENT NO. : 5,681,559

DATED : October 28, 1997

INVENTOR(S) : David DiGiusto and Anne H.M. Galy

It is certified that error appears in the above-indentified patent and that said Letters Patent is hereby corrected as shown below:

Column 16, line 28, after "(1992)" insert --*Blood* 79:1704-1711--
line 64, "CD3.4" should be --CD34--
Column 17, line 62, "4" should be --6--
Column 18, line 3, "176" should be --174--
line 14, after "(1991)" insert --*J. Exp. Med.* 174:1283-1286--

Signed and Sealed this

Twenty-eighth Day of July, 1998

Attest:

BRUCE LEHMAN

Attesting Officer

Commissioner of Patents and Trademarks